United States Patent [19]

Reischl et al.

[11] Patent Number: 5,474,916
[45] Date of Patent: Dec. 12, 1995

[54] PROMOTOR CONTROLLED SPECIFIC AMPLIFICATION OF NUCLEIC ACID SEQUENCES

[75] Inventors: Udo Reischl, Grafenau; Ruediger Rueger, Seeshaupt; Cortina Kaletta, Munich; Christoph Kessler, Dorgen; Joerg Kleiber, Penzberg, all of Germany

[73] Assignee: Boehringer Mannheim GmbH, Mannheim, Germany

[21] Appl. No.: 950,849

[22] Filed: Sep. 28, 1992

[30] Foreign Application Priority Data

Sep. 26, 1991 [DE] Germany ............................ 41 32 132.4
Apr. 21, 1992 [DE] Germany ............................ 42 13 029.8

[51] Int. Cl.$^6$ .................... C12P 19/34; C12Q 1/68; C07H 21/04
[52] U.S. Cl. ......................... 435/91.2; 435/6; 536/24.1
[58] Field of Search .................. 435/6, 91.2; 536/24.1; 935/16, 78

[56] References Cited

U.S. PATENT DOCUMENTS

| | | | |
|---|---|---|---|
| 5,112,734 | 5/1992 | Kramer et al. | 435/6 |
| 5,194,370 | 3/1993 | Baninger et al. | 435/6 |
| 5,215,899 | 6/1993 | Dattagupta | 435/6 |

FOREIGN PATENT DOCUMENTS

| | | |
|---|---|---|
| 0369775 | of 0000 | European Pat. Off. . |
| 0292802 | of 0000 | European Pat. Off. . |
| 0200362 | of 0000 | European Pat. Off. . |
| 0310229 | of 0000 | European Pat. Off. . |
| 0427073 | of 0000 | European Pat. Off. . |
| 0329822 | of 0000 | European Pat. Off. . |
| 0373960 | of 0000 | European Pat. Off. . |
| 0427074 | of 0000 | European Pat. Off. . |
| WO88/10315 | of 0000 | WIPO . |
| 8901050 | 2/1989 | WIPO . |
| 8906700 | 7/1989 | WIPO . |

OTHER PUBLICATIONS

Urdea et al., Nucl. Acid. Res 16: 4937–4956 (1988) "A Comparison of Non–Radiosotipic Hybridization Assays . . . ".
Pollard–Knight., J. Meth. Cell Mol. Biol. 2: 113–132 (1990) "Current Methods in Nonradioactive . . . ".
Nucl. Acids Res. 15, 8773–8798 (1987).
Biochemistry 1987, 26, 2690–2696.
Biochem. Biophys. Res. Commun.159, 297–304 (1989).
Gene Anal. Techn. 6, 29–32 (1989).
Biochem. J. 224, 799–815 (1984).
J. Bacteriol.170, 5248–5256 (9188).
Biophysical Chemistry III,1183–1211, ed. Freeman and Company.
FEBS letters 212,271–275 (1987).

Primary Examiner—Margaret Parr
Assistant Examiner—Eggerton Campbell
Attorney, Agent, or Firm—Nikaido, Marmelstein, Murray & Oram

[57] ABSTRACT

Process for the specific production of nucleic acids based on the principle of transcription in which a promoter oligonucleotide and a template-specific oligonucleotide which can hybridize with it are used as a promoter reagent and a process for nucleic acid detection which is based on this process.

25 Claims, 22 Drawing Sheets

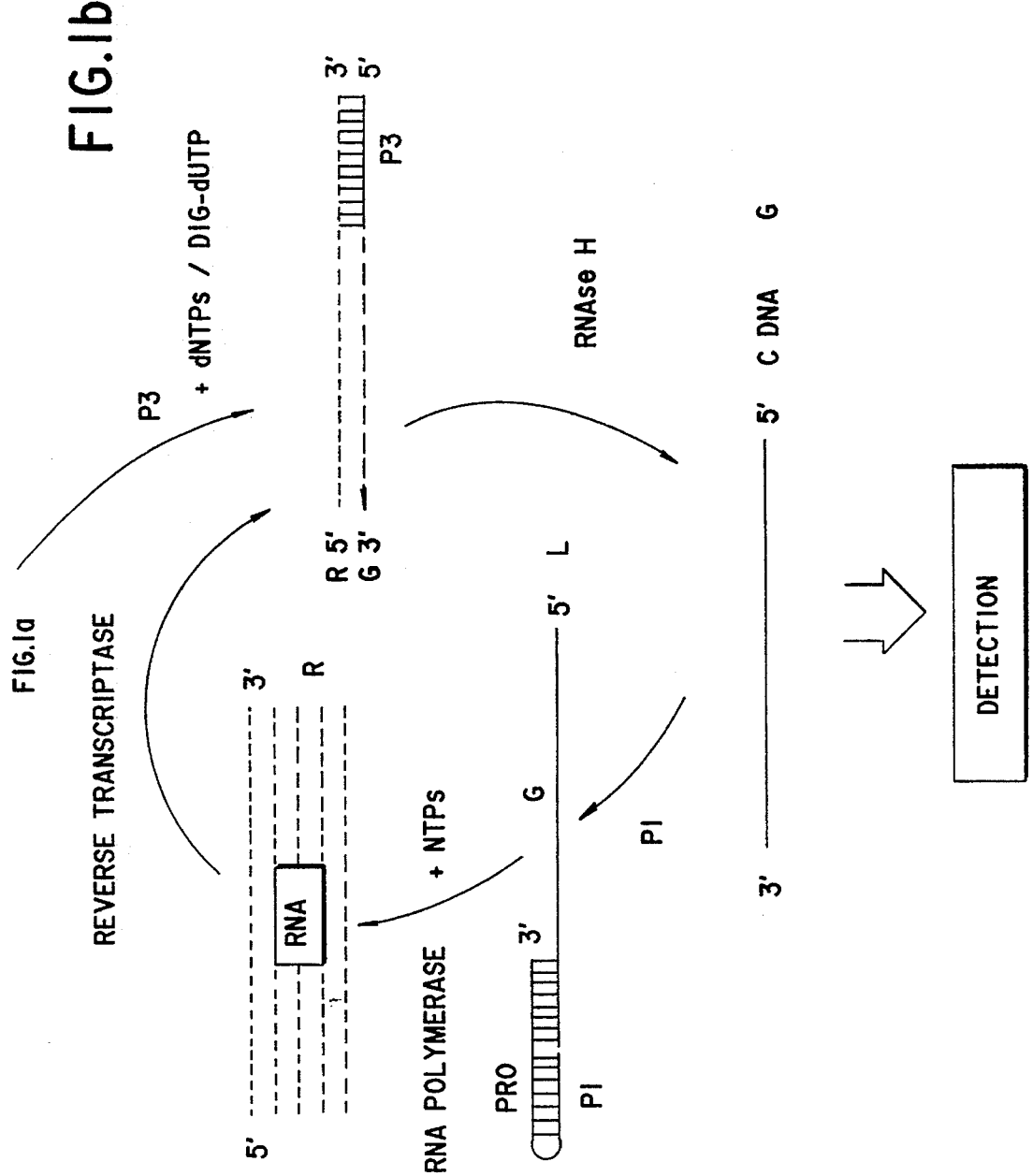

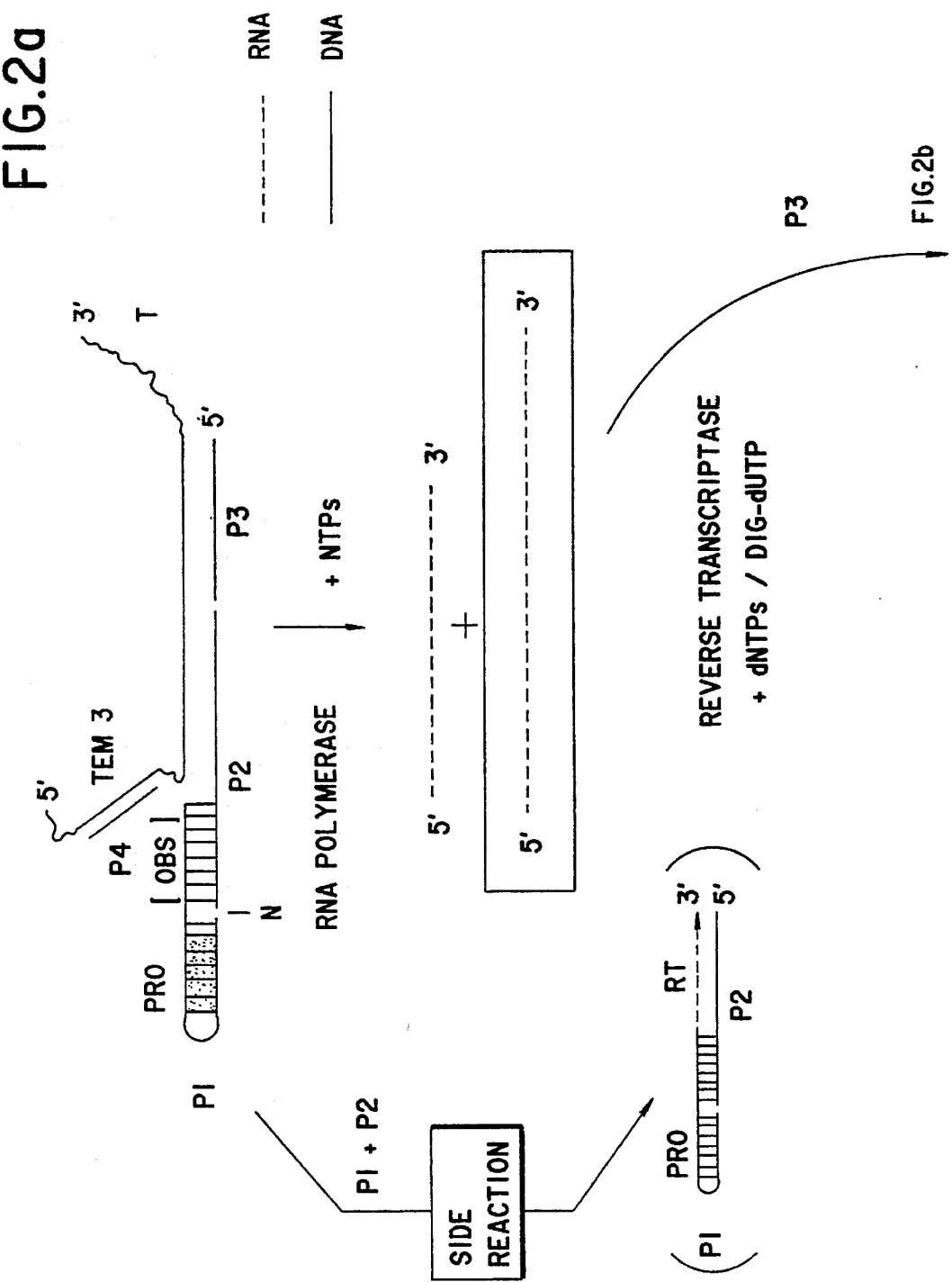

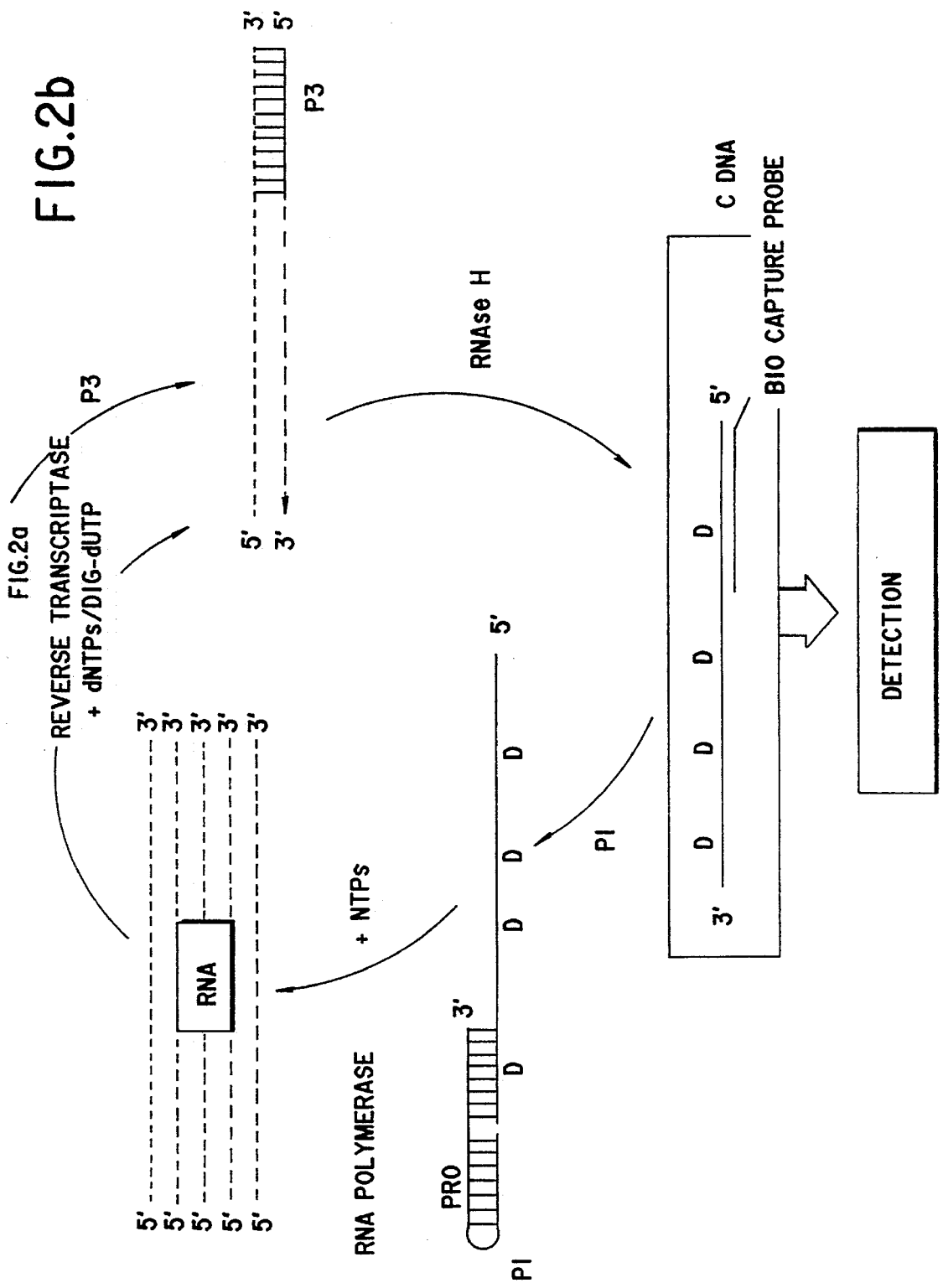

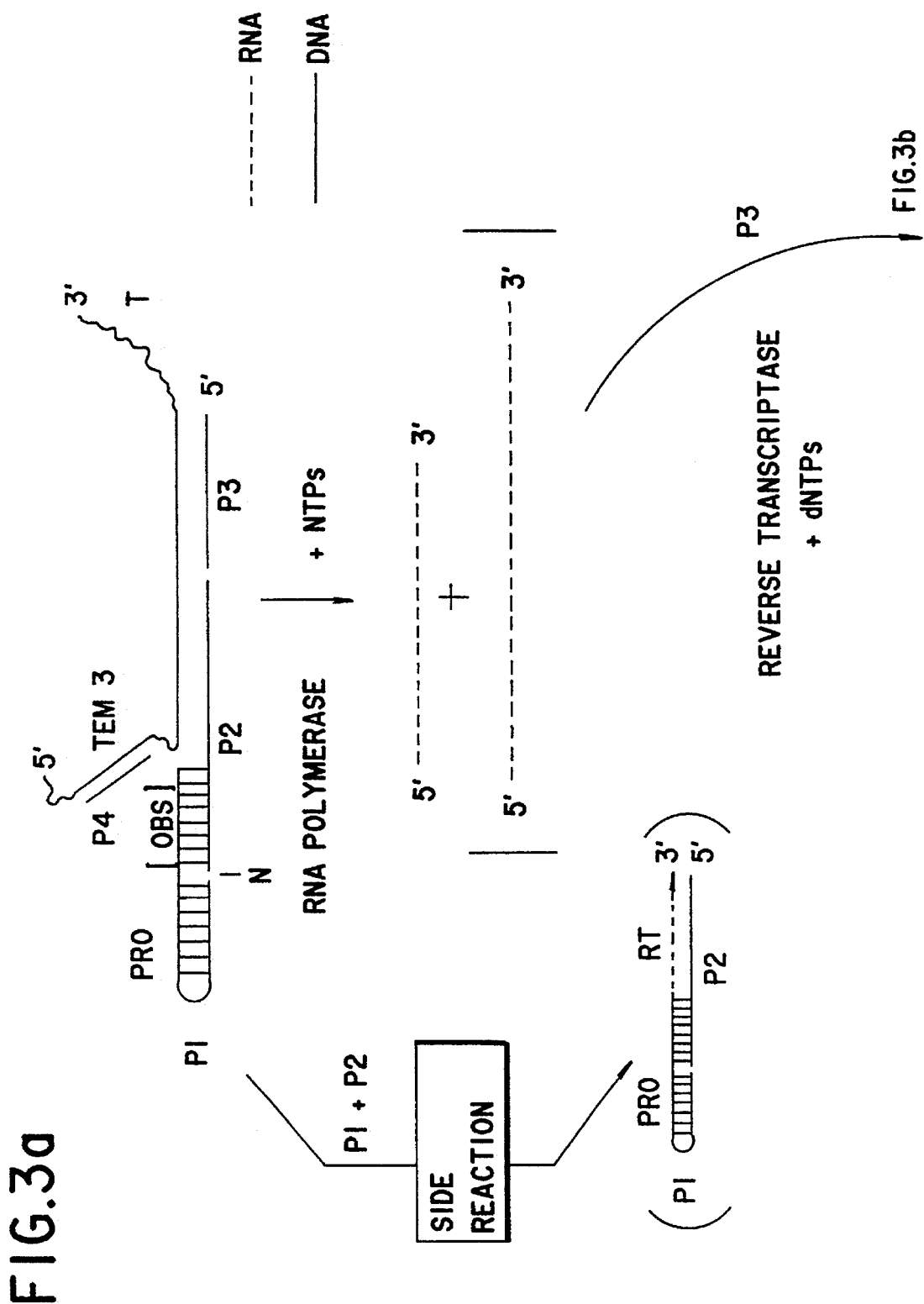

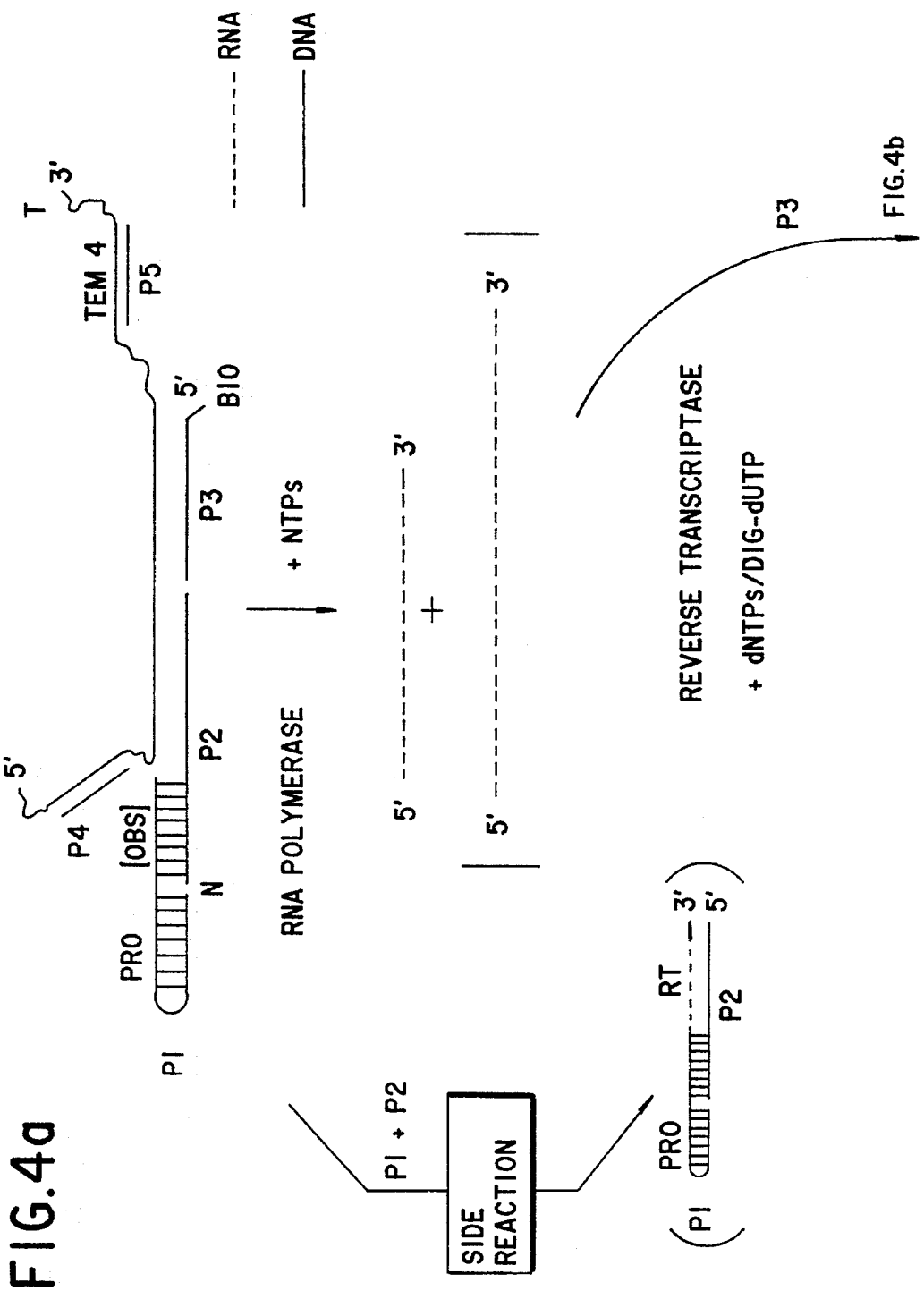

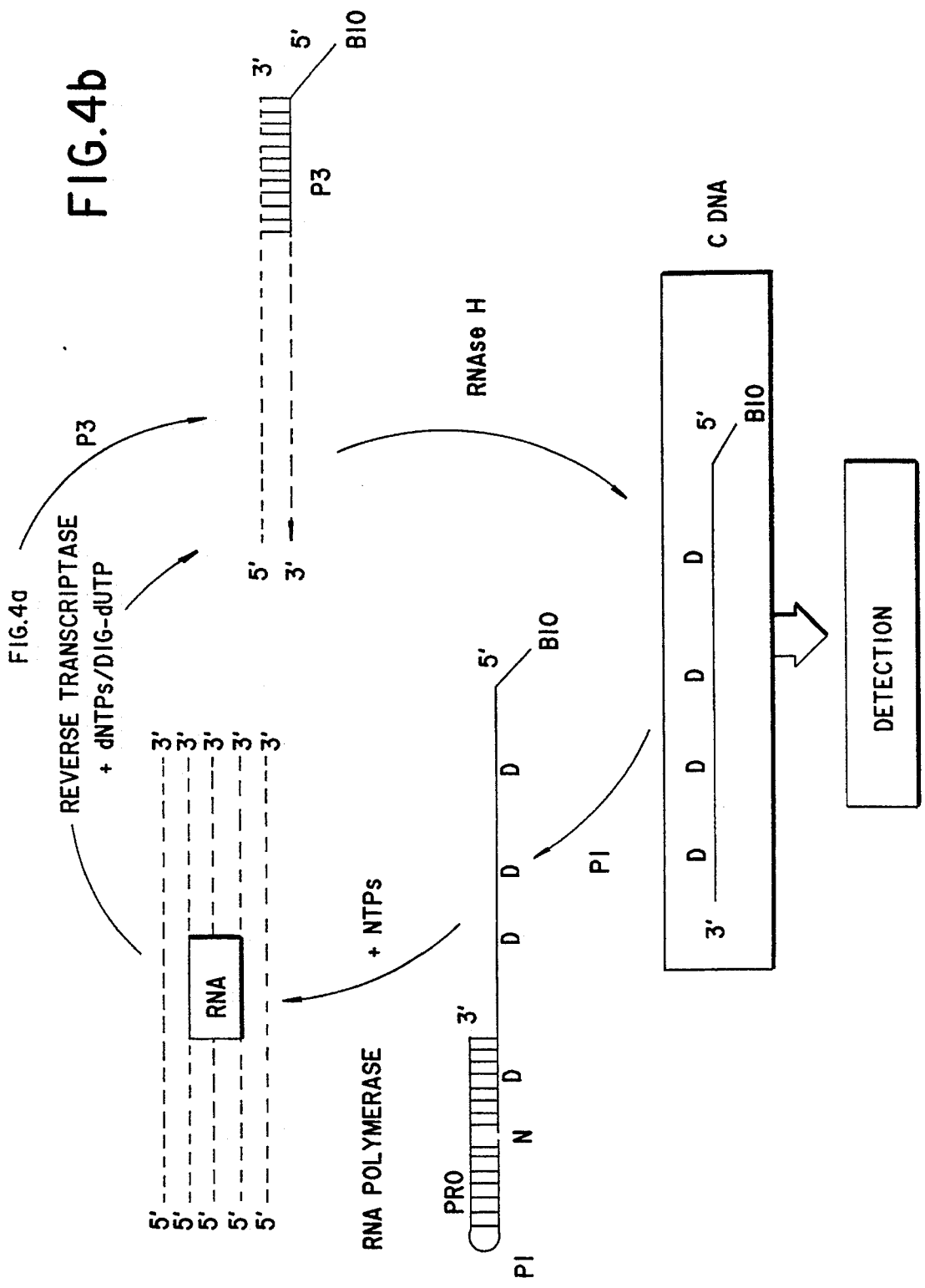

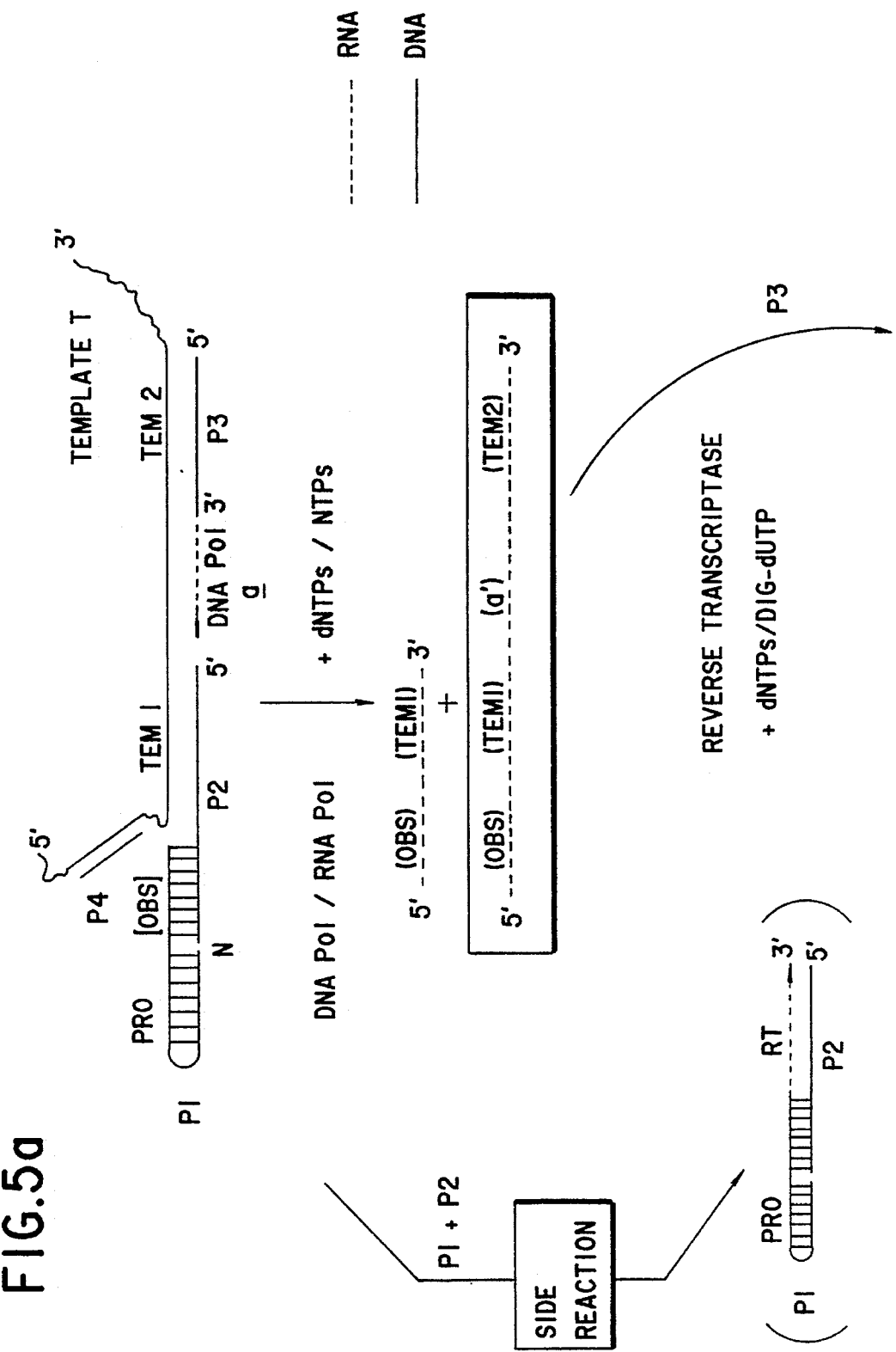

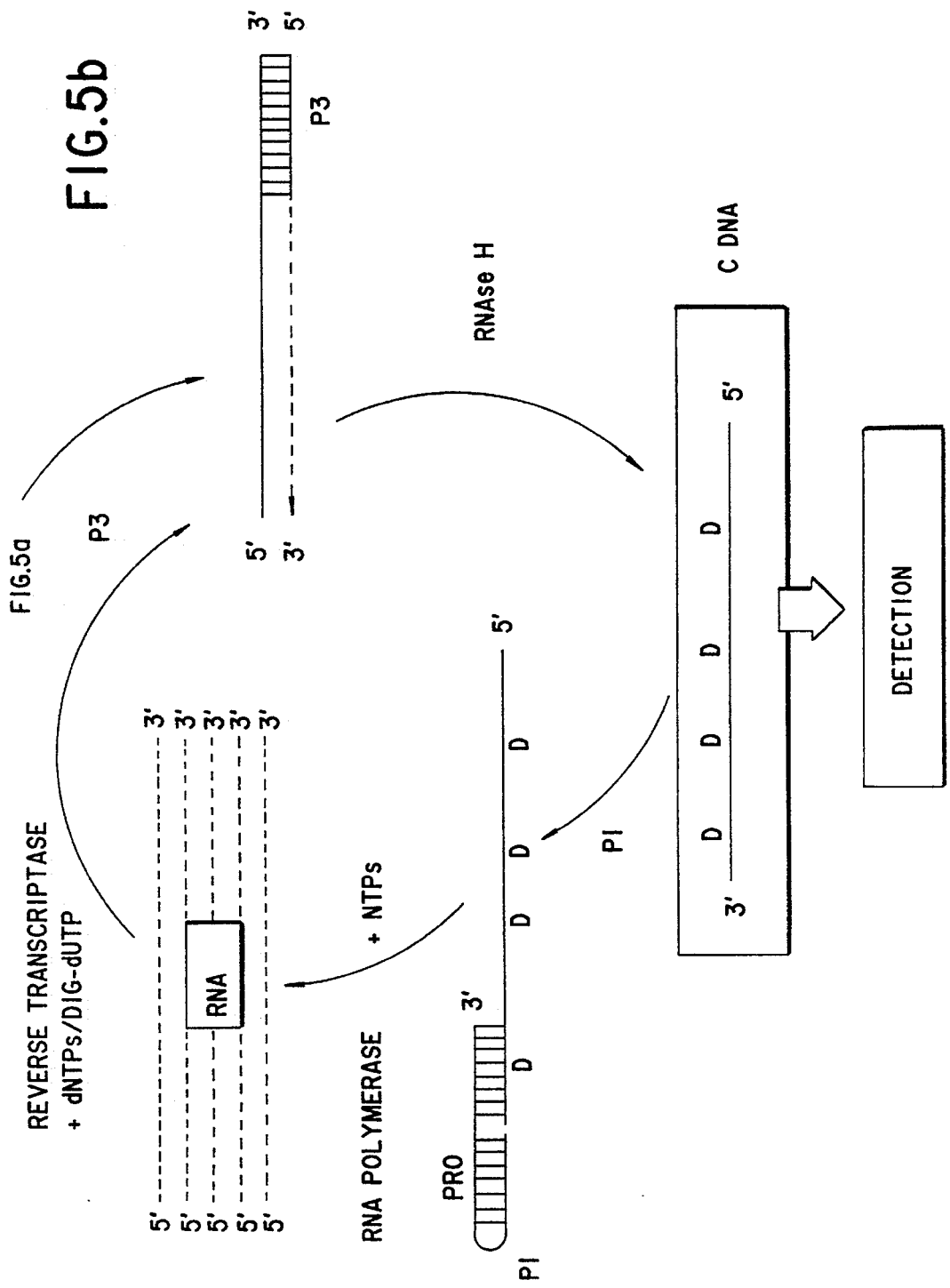

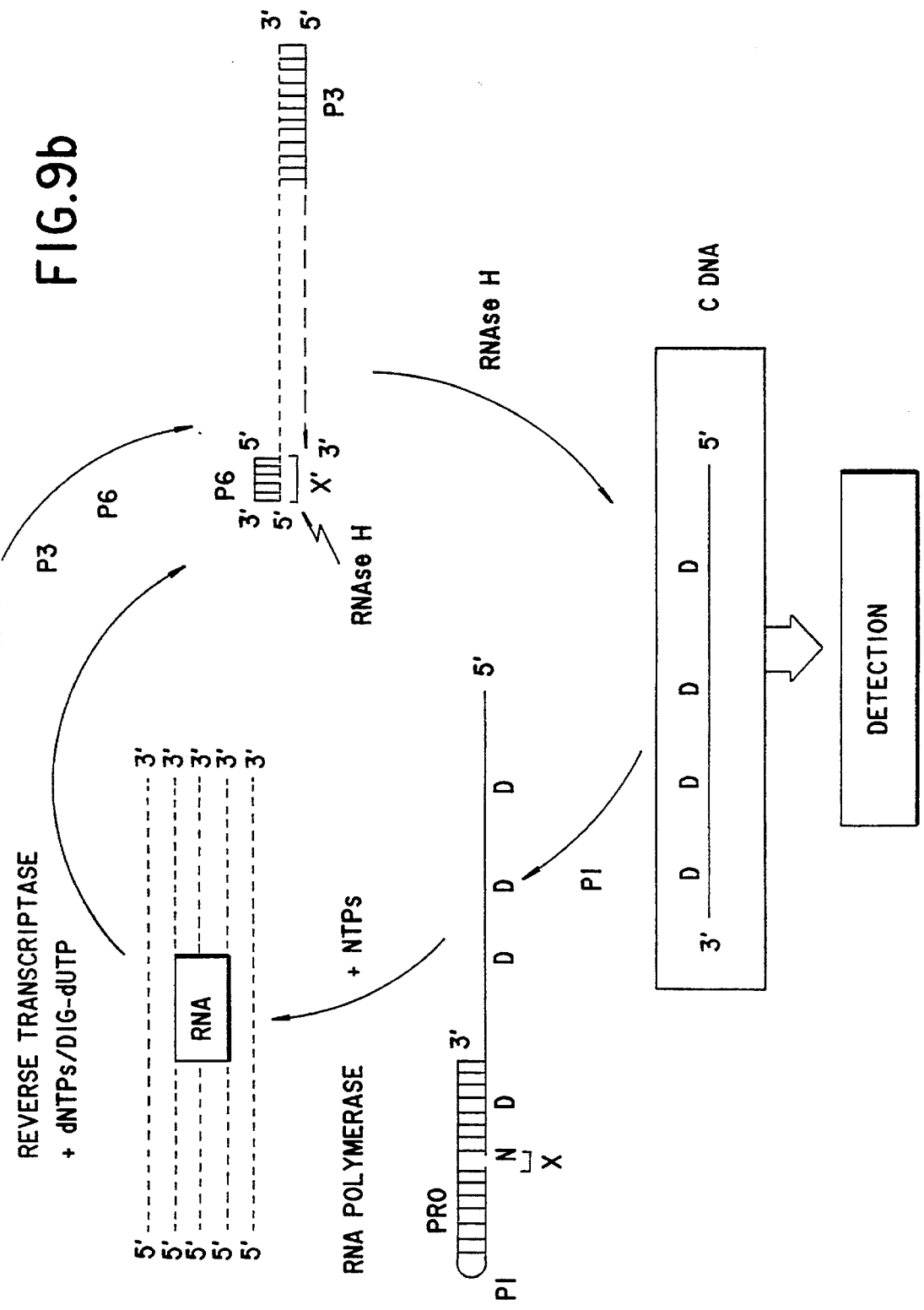

FIG.11

```
        P1 (106mer)
T T  AATTAATACGACTCACTATAGGGCGCTCGCCGCTAGCGTACGACGACTGGAGTACTGGACATGCT  3'
T T  TTAATTATGCTGAGTGATATCCCGAGCGGCGATCG                                5'
         PRO
```

FIG.14

3' CCGCGAGCGGGCGATCG 5'

P6 (16mer)

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO: 1:

GCUUGAUCCG GCUACCUGCC CAUUCGACCA CCAAGCGAAA CAUCGCAUCG AGCGAGCACG    60

UACUCGGAUG GAA    73

( 2 ) INFORMATION FOR SEQ ID NO: 2:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 2:

AGTGAGTCGT ATTAATTTTT TTTAATTAAT ACGACTCACT ATAGGCGCTC GCCGCTAGCG    60

TACGACGACT GGAGTACTGG ACATGCT    87

( 2 ) INFORMATION FOR SEQ ID NO: 3:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 3:

TGGTCGAATG GGCAGGTAGC AGCATGTCCA GTACTCCAGT CGTCGTACGC TAGCGGCGAG    60

CGCCTAT    67

( 2 ) INFORMATION FOR SEQ ID NO: 4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

CGATGCGATG TTTCGCTTGG    20

( 2 ) INFORMATION FOR SEQ ID NO: 5:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 5:

GCTAGCGGCG AGCGCCTATA GTGAGTCGTA TTAATTTTTT TTAATTAATA CGACTCACTA    60

TAGGCGCTCG CCGCTAGCGT ACGACGACTG GAGTACTGGA CATGCT    106

( 2 ) INFORMATION FOR SEQ ID NO: 6:

( i ) SEQUENCE CHARACTERISTICS:
        ( A ) LENGTH: 48 base pairs
        ( B ) TYPE: nucleic acid
        ( C ) STRANDEDNESS: single -continued ( D ) TOPOLOGY: linear ( i i ) MOLECULE TYPE: cDNA ( x i ) SEQUENCE DESCRIPTION: SEQ ID NO: 6:

TGGTCGAATG GGCAGGTAGC AGCATGTCCA GTACTCCAGT CGTCGTAC  48

( 2 ) INFORMATION FOR SEQ ID NO: 7:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO: 7:

GCTAGCGGCG AGCGCC  16

( 2 ) INFORMATION FOR SEQ ID NO: 8:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO: 8:

CACATCATCC TGATCGACAA  20

PROMOTOR CONTROLLED SPECIFIC AMPLIFICATION OF NUCLEIC ACID SEQUENCES

The invention concerns a process for the specific production of nucleic acids and a process for the specific detection of nucleic acids as well as reagents for carrying out both these processes.

Nucleic acids acting as information carriers, are the basis for specific life forms for all organisms known up to now. They code for proteins; however, some nucleic acids probably also have catalytic or structural effects. Nucleic acids, because of their specificity, can also be used to differentiate between and to detect organisms. The individual nucleic acids are, however, only present in organisms in a very limited amount. It has therefore proven to be advantageous for the practical handling of nucleic acids to generate multiple copies of these nucleic acids in vivo (cloning) or in vitro (amplification). While the former method is time-consuming and complicated, the in vitro amplification has developed into a practical alternative in recent years.

A process is described in EP-A-200 362 which concerns an amplification of a part of a starting nucleic acid which proceeds in cycles. In each cycle an opposite strand is formed to each of the nucleic acids present. However, the reaction procedure results in a relatively large number of cycles.

One attempts to circumvent this disadvantage using processes based on transcription steps which lead to a multitude of copies in cycles. Such a process is for example described in EP-A-0 310 229. In this process an oligonucleotide (promoter primer) which contains a template-specific region as well as a T7 promoter sequence is elongated on the template nucleic acid with mononucleotides. An opposite strand is then formed by means of a second primer. During this an opposite strand is also formed to the previously single-stranded promoter region and therefore the functionality of the promoter is restored. Afterwards a promoter-controlled transcription of the hybrid formed takes place. cDNA corresponding to the transcript RNA molecules formed is produced by means of an opposite strand primer. The hybrid is denatured and the cDNA is again reacted with promoter primer. Elongation of this primer on the cDNA again leads to a hybrid which contains a functional promoter. This molecule can also be introduced into the transcription cycle. A disadvantage of this reaction sequence is the fact that two elongation reactions are necessary to produce a transcribable molecule. The same problems also occur in the processes of WO 88/10315 and EP-A-0 329 822 as well as EP-A-0 373 960.

A process is proposed in EP-A-0 427 074 in which the template nucleic acid is reacted directly with a template-specific primer containing a promoter to directly form a transcribable molecule. The subsequent transcription yields RNA, one part of which corresponds to partial sequences of the template nucleic acid and the other part of which is complementary to a further sequence located on the primer. A process is also described in this patent application in which two different primers are used which are ligated on the template nucleic acid in the hybridized state whereby an elongated transcribable molecule is formed. A disadvantage of these processes is that transcription products of the overhanging 5' region of the promoter primer are formed even in the absence of template nucleic acids. This results in a background signal which is only dependent on the amount of promoter primer present (unspecific amplification, loss in sensitivity). For this reason the reaction described in EP-A-0 427 074 can only be used with difficulty as a starting reaction for cyclical reactions based on transcriptions. Namely it has been shown that the concentration of the promoter primer must be very much higher than the template nucleic acid concentration since the promoter primer is consumed in each cycle.

Another reaction for the synthesis of a transcribable nucleic acid is described in EP-A-0 369 775 and EP-A-0 427 073. In this process the 3' end of the template nucleic acid is ligated to the 5' end of a promoter primer. The template is bound to the promoter primer by hybridization with the template-specific sequence of the overhanging 3' end. This reaction therefore also requires an enzymatic reaction for the production of the transcribable molecule. Moreover it has the disadvantage that only template nucleic acids with a defined 3' end can be detected.

The object of the present invention was therefore to provide an amplification process based on a transcription reaction which avoids the disadvantages of the state of the art. In particular it should yield a product in a few steps which can be used in a transcription cycle and reduce the sensitivity problems which occur when promoter primers are used in the transcription.

This object is achieved by the invention described in the following.

The invention concerns a process for the specific production of nucleic acids by reaction of a promoter reagent P with a template nucleic acid T with formation of a transcribable nucleic acid complex K and promoter-controlled transcription with formation of transcripts R, in which the promoter reagent P contains a promoter oligonucleotide P1 and a template-specific oligonucleotide P2 which hybridizes to P1. A further subject matter is a process for the specific detection of nucleic acids which is based on the process for producing nucleic acids according to the present invention and reagents which are suitable for carrying out these processes.

The process according to the present invention is a special embodiment of the so-called hybridization tests, the essential features of which are known to one skilled in the area of nucleic acid diagnostics. To the extent that experimental details are not set forth in the following, reference is made in full detail to "Nucleic acid hybridisation", published by B. D. Hames and S. J. Higgins, IRL Press, 1986, in particular in chapters 1 (Hybridisation Strategy), 3 (Quantitative Analysis of Solution Hybridisation) and 4 (Quantitative Filter Hybridisation), Current Protocols in Molecular Biology, Edt. F. M. Ausubel et al., J. Wiley and Son, 1987, in particular 2.9.1.–2.9.10 and Molecular Cloning, Edt. J. Sambrook et al., CSH, 1989, in particular 9.4.7.– 9.5.8. These in particular include the known methods for the production of labelled nucleoside triphosphates which are also described in EP-A-0 324 474, the chemical synthesis of modified and unmodified oligonucleotides, the cleavage of nucleic acids by means of restriction enzymes, the choice of hybridization conditions by which means a specificity can be achieved which is dependent on the extent of homology between the nucleic acids to be hybridized, their GC content and their length, as well as the formation of nucleic acids from nucleoside triphosphates with the aid of polomerases, if necessary also by using so-called primers.

A label within the sense of the present invention consists of a directly or indirectly detectable group L. Examples of directly detectable groups are radioactive ($^{32}P$), coloured or fluorescent groups or metal atoms. Indirectly detectable groups are for example immunologically or enzymatically active compounds such as antibodies, antigens, haptens or enzymes or enzymatically active parts of enzymes. These are detected in a subsequent reaction or reaction sequence. Haptens are particularly preferred since nucleoside triphosphates (rNTP or dNTP) labelled with them can in general be used particularly well as substrates for (PNA or DNA) polymerases and it is easy to carry out a subsequent reaction with a labelled antibody against the hapten or the haptenized nucleoside. Such nucleoside triphosphates are for example bromonucleoside triphosphates or digoxigenin-, digoxin- or fluorescein-coupled nucleoside triphosphates. The steroids mentioned in EP-A-0 324 474 and their detection have proven to be particularly suitable. With regard to their incorporation into nucleic acids reference is hereby made to EP-A-0 324 474.

A specific production process or test is understood as a process by which means certain nucleic acids can be produced or detected selectively, if desired, also in the presence of other nucleic acids. It is, however, also possible to make the object of the process the production or detection of several nucleic acids or a group of nucleic acids with a partially corresponding or similar nucleotide sequence, or several sections of a nucleic acid in the presence of other nucleic acids. Either of the two complementary strands can be used for the detection of double-stranded nucleic acids.

An essentially complementary nucleic acid or nucleic acid sequence is understood as nucleic acids or sequences which can hybridize with the corresponding nucleic acid and have a nucleotide sequence in the hybridizing region which is either exactly complementary to the other nucleic acid or differs by only a few bases from the exactly complementary nucleic acid. In this case the specificity depends on the degree of complementarity as well as on the hybridization conditions. Oligonucleotides which are essentially complementary to a part of a template nucleic acid are denoted template-specific in the following.

The basis of the process according to the present invention are samples which contain nucleic acids which are purified or combined with other components, in particular with other nucleic acids. The sample can contain further constituents such as proteins, salts etc. Using the process according to the present invention it is possible to amplify nucleic acid sequences if these sequences are present in a nucleic acid present in the sample. The nucleic acid which is intended to form the basis for the production of other nucleic acids according to the present invention is denoted template nucleic acid (or template) in the following.

Nucleic acids can be produced with the process according to the present invention which contain the entire nucleotide sequence information of the template nucleic acid but preferably contain only parts thereof. In order to amplify partial sequences of the template nucleic acid it is not necessary, but possible, to fragment the template nucleic acid before carrying out the process.

In order to carry out the process the template nucleic acid must be present as a single strand. This is normally the case for RNA without further pretreatment. In the case of DNA a double-stranded template nucleic acid can be made single-stranded by denaturation in a known manner.

In the following a reagent is denoted as promoter reagent P which has functional promoter sequences as well as template-specific sequences. The promoter reagents of the state of the art are composed of an oligonucleotide with a promoter region and a template-specific region.

In contrast the promoter reagent of the invention contains a promoter oligonucleotide and a template-specific oligonucleotide which can hybridize with each other.

A promoter oligonucleotide P1 within the sense of the invention is a nucleic acid which contains in the upstream region a substantially and preferably completely double-stranded region PRO which starts the synthesis of RNA by recognizing and binding RNA polymerase. This PRO region contains a sequence which initiates the transcription of the nucleic acid region adjoining this sequence in the 5' direction by a RNA polymerase. The double-stranded PRO sequence preferably has a length of 17–100 bases, particularly preferably 17–50 bases. Suitable double-stranded sequences which can bind a RNA polymerase are described for example in Nucleic Acids Research 12, pages 7035–7056 (1984) and in Protein Sequences and DNA Analysis 1, pages 269–280 (1988), Biophysical Chemistry, Part III, p. 1183–1211, Freeman & Co., San Francisco, 1980; J. Bacteriol 170, p. 5248–5256 (1988); Biochem. J. 224, p. 799–815 (1984); Gene Acal. Techn. 6, p. 29–32 (1989), EP-A-0 292 802 and Nucleic acid probes, ed. Symons (CRC Press, Boca Raton, 1989). The two strands of the double-stranded portion can either be present in an open form or can be linked upstream in the form of a hairpin structure (loop). The hairpin region linking the complementary single strands is preferably 5–50 nucleotides and particularly preferably 5–10 nucleotides long, and is preferably composed of only one type of nucleotide in order to prevent the formation of base pairs. The promoter oligonucleotide P1 has a single-stranded region OBS at the downstream 3' end. This region is either not at all or only to a limited extent complementary to the template nucleic acid and to other nucleic acids present in the sample which are not to be processed according to the present invention so that it cannot hybridize directly with these nucleic acids. The OBS region is preferably 6 to 50 nt, particularly preferably 12 to 30 nt long.

The double-stranded promoter region PRO can be separated from the oligonucleotide binding site OBS by a sequence of further nucleotides. In addition a further nucleotide sequence can adjoin the region OBS in the downstream 3' direction.

The 3' end of the promoter oligonucleotide P1 is preferably non-phosphorylated while the 5' end can be phosphorylated or non-phosphorylated. The promoter oligonucleotide P1 can in addition contain a further nucleotide sequence in the downstream direction adjoining the sequence PRO. These are preferably nucleotide sequences which are complementary to the corresponding opposite strand. Sequences which promote transcription are preferred (Nucl. Acids Res. 15, p. 8783–8798 (1987)). These are preferably 1–10 nt. They can, however, be nucleotides which allow additional reaction steps (e.g. ori sequences, RNA replication recognition site, restriction cleavage site).

The template-specific oligonucleotide P2 contains a single-stranded nucleotide sequence TEM 1' which is essentially complementary to a nucleotide sequence of the template nucleic acid and can therefore hybridize with this sequence. This sequence is preferably 6 to 50 nt long, particularly preferably 12 to 30 nt long. The specificity of the production process according to the present invention can be controlled by its length and complementarity. For example by suitable choice of this sequence it is possible to specifically make only one or several template nucleic acids in the sample the object of the process according to the present invention and to amplify its sequence.

The template-specific oligonucleotide P2 additionally contains a nucleotide sequence OBS' which can specifically hybridize with the sequence OBS of promoter P1. This sequence OBS' is preferably essentially complementary to the sequence OBS. The sequence TEM 1' is preferably located in the 5' terminal region of the oligonucleotide P2 while the sequence OBS' is preferably in the 3' terminal region of P2. There can be additional sequences between them. P2 can contain additional nucleotide sequences upstream of OBS' which correspond to a portion of PRO. An essential feature of the invention is the fact that the 3' end of the oligonucleotide P2 is not covalently linked to the 5' end of the promoter oligonucleotide P1. Under hybridization conditions for the sequence OBS/OBS' there is no covalent bond between the 3' end of P2 and the 5' end of P1 which faces it. There can for example be a nick at this site. The nick can be at position −5 to +30 in relation to the transcription initiation site. The nick is preferably in the region −5 to −1 or +15 to +30 when the initiation site is designated as position +1. OBS is preferably 6–50 nt, particularly preferably 12–30 nt long.

In a first step of the process according to the present invention for the specific production of nucleic acids, the sample, which contains the template nucleic acid, is reacted with the promoter reagent P under hybridization conditions. In this process a transcribable nucleic acid complex K is formed in which the template nucleic acid is hybridized to the oligonucleotide P2 via a double-stranded region TEM 1/TEM 1' and this in turn is hybridized to the promoter via a double-stranded region OBS/OBS'.

The specificity and sensitivity of the process according to the present invention can be considerably increased by the use of a further oligonucleotide P3. It is preferably used simultaneously with the promoter reagent, and together with this and T forms the transcription complex K. It is in principle possible to hybridize further oligonucleotides to the template nucleic acid in the 3' direction which have the same function as P3. Primer P3 hybridizes to a nucleotide sequence TEM 2 of the template nucleic acid which is located in the 3' direction of the template nucleic acid. For this, primer P3 has a single-stranded nucleotide sequence TEM 2' in the 3' region which is essentially complementary to TEM 2. The TEM 1 region is different from the TEM 2 region of the nucleic acid. The regions TEM 1 and TEM 2 are preferably directly adjacent on the template nucleic acid so that they are only separated by a nick. They can, however, also be separated from one another by 1–1500, preferably 1–150 nt. This gap (a) can then, preferably before starting the transcription, be closed by the activity of a DNA-dependent DNA polymerase or RNA-dependent DNA polymerase such as e.g. reverse transcriptase. The gap does not have to be completely closed by this elongation activity; short gaps of 1–5 nucleotides between the 5' end of P2 and the 3' end of P3 still result in the formation of a transcription product which contains the sequences from P2, the elongated sequence (a') and P3. In the hybridized state the 5' end of the oligonucleotide P2 and the 3' end of the primer P3 or the elongated end are directly adjacent to one another but are, however, not covalently linked to one another. The primer P3 can contain further nucleotides in addition to the sequence TEM 2' which do not hybridize with the template nucleic acid. Such a sequence could for example be an ori sequence (start region for a replication), a RE cleavage site, a replicase-specific sequence or a binding region for a sequencing primer or a binding protein. P3 preferably has an OH group at its 5' and 3' ends. The hybridization regions TEM 1, TEM 2, and TEM 3 and TEM 4 which are described later, are preferably 6–50 nt and particularly preferably 12–30 nt long.

A major advantage of the present invention is that the amount of the promoter oligonucleotide P1 can be maintained independent of the amount of template-specific sequences (oligonucleotide P2). An essential finding of the invention is namely that the sensitivity in subsequent cyclical transcription reactions can be increased compared to the state of the art when the amount of template-specific sequences is only relatively small in comparison to promoter sequences. The stoichiometry of the amount of P1 to P2 used is preferably 100:1 to 2:1, particularly preferably 50:1 to 5:1. The concentration of the promoter oligonucleotide P1 then essentially depends on how large the number of nucleic acids which are to be produced should be. A high ratio of the amount of primer P3 to P2 is also selected, preferably 100:1 to 2:1, particularly preferably 50:1 to 5:1. The concentration of P3 is related primarily to the concentration of P1. The concentrations of P1 and P3 are preferably about the same.

The nucleic acid complex K which is formed in this way is now subjected to a promoter-controlled transcription. The conditions under which a promoter-controlled transcription can proceed are the same for this complex as for the transcription reactions of the state of the art (see e.g. EP-A-0 369 775). They depend on the chosen promoter/polymerase system. Examples of promoter systems are known from T7, SP6, N4 and T3. (For N4 see RNA Polymerase and the Regulation of Transcription, Ed. Reznikoff, Elsevier Science, 1987, pages 37–45). Basically a RNA polymerase and ribonucleoside triphosphates (rNTPs) are required. The transcription system of T7 (T7 RNA polymerase and T7-specific promoter) has proven to be a particularly preferred transcription system.

The T7 RNA polymerase-promoter-specific complementary sequence regions within the double-stranded region of the primer P1 can be between 12 and 20 nucleotides long (described by Milligan et al. (1987), Nucl. Acids Res., 15, p. 8783–8798). However, it preferably has a length of 17 nucleotides. For example the transcription by T7 RNA polymerase begins at position +1 (Fig. on page 2690 in Biochemistry 1987, 26, 2690–2696). The transcription is preferably initiated when +1 and +2 in the sequence of the primer P1 represent C. Further details are described in "Gentechnologie von A-Z" pages 222–223 (Verlag VCH, Weinheim 1990, under the heading "Gene"). In addition reference is also made to Proc. Natl. Acad. Sci. USA 83, 3614 (1986) and Gene 72, p. 75 (1989). Reference is made expressly to the content of these publications.

An essential finding of the process according to the present invention is that the promoter-controlled transcription of such double-stranded nucleic acids which have single-stranded breaks in the double-stranded region is also possible. Moreover it was astounding that these single-stranded breaks can also be located within the promoter sequence.

Products of the transcription are RNA transcripts. The main product is an RNA R whose 5' end is located at the transcription starting point and whose 3' end is at the 5' terminal position of the TEM 2' region. This RNA in particular contains the OBS sequence as well as sequences which are homologous to TEM 1 and TEM 2.

The product of the non-specific transcription of the hybridization product of P1 and P2, which also represents a transcribable nucleic acid complex K', is only formed in comparatively small amounts in the process according to the present invention since the amount of this complex is also small because of the small amount of oligonucleotide P2 present. This short transcript would in certain circumstances interfere with the subsequent transcription reactions.

The transcript R which forms as the main product can be the final product of the process according to the present invention for the production of nucleic acids. The purpose of the production process can then for example be to increase the number of nucleic acids having the same sequence information before a subsequent cloning or in the case of the incorporation of detectably-labelled mononucleotides, the production of detectable nucleic acid probes (defined length) for carrying out hybridization assays.

However, this transcript is preferably amplified further in a cyclical reaction process. The reaction steps necessary for this are in principle known from the state of the art. The sequence of reactions described in the following has, however, proven to be particularly preferred.

For this reaction the mixture from the first transcription stage is firstly subjected to conditions under which a cDNA (opposite strand G) is formed from the main product of the transcription. This can be achieved in a simple and preferred manner by addition of reverse transcriptase and deoxyribonucleotides (dNTPs) if P3, which is complementary to TEM 2 on the RNA, is already present in the reaction mixture in an adequate concentration. P3 then acts as a primer which is elongated enzymatically using R as the template to form G. Since P3 can only hybridize with the transcripts R that have been formed from a transcription complex K but not with the transcripts which could have been formed as a by-product from the template-unspecific transcription complexes, e.g. only from P1 and P2, the use of P3 leads to a considerable increase in selectivity. It is also possible to use one or several further oligonucleotides P7 . . . PN which, in the same way as P3, can hybridize downstream of and adjoining P3 to the template nucleic acid; these oligonucleotides can also serve as a primer to synthesize the opposite strand or/and as capture probe or detection probe.

In a preferred embodiment, modified deoxyribonucleotides such as digoxigenin-dUTP can also be incorporated into the cDNA. In a subsequent step the RNA portion of the RNA/DNA double-strand formed is digested enzymatically e.g. by RNAse H. The cDNA synthesized with the aid of this RNA remains as a template.

The 3' terminal region of this cDNA has in turn the sequence OBS'. Hence under hybridization conditions promoter oligonucleotide P1 can hybridize directly with this cDNA via OBS to form a transcribable nucleic acid complex L. It should be noted that in this case the oligonucleotide P2 which is only present in a limited amount is no longer necessary for the formation of this transcribable complex.

As a result of the ratio of the amounts of P1/P2 oligonucleotide P2 only competes to a minor extent with the cDNA for binding to the promoter oligonucleotide P1. The yields of transcribable products L are therefore comparably high.

In a further step the promoter-controlled transcription of the nucleic acid complex L takes place. For this it is not necessary to again add reagents since these are already present in the reaction mixture from the starting reaction. It is, however, in principle possible to add reagents, for example when the reagent has been consumed. The result of the transcription is a multitude of RNA transcripts R which are available for the renewed formation of cDNA.

The said cycle can be continued until the desired number of nucleic acids has been formed.

The product of the production process according to the present invention can be any of the intermediate products formed in the cycle, i.e. the transcripts R, the hybrid of R and cDNA, the cDNA itself, the hybrid of P1 and cDNA or the mixture itself. In a preferred embodiment modified ribonucleotides e.g. digoxigenin-UTP can also be incorporated into the intermediate product R.

The products can be purified or/and processed further in a known manner.

In order to test whether an adequate number of nucleic acids has been formed, a detectably labelled detector probe is for example added which can hybridize with the desired product and the hybrid is detected or the nucleic acids formed can be directly detected by incorporation of detectably labelled mononucleotides.

An advantage of the process according to the present invention is that it can proceed isothermally i.e. it can be carried out at one temperature. A further advantage is that a possible side reaction in which the hybrid of promoter oligonucleotide P1 and oligonucleotide P2 binds to the newly formed template-specific transcripts R is inhibited by completing the partial double strand with reverse transcriptase. Another advantage of the process according to the present invention is that different nucleic acids can be detected using only a single promoter oligonucleotide P1 since the template-specific sequence is located on the oligonucleotide P2 which is separate from it and thus can be varied independently (with OBS remaining the same).

In an embodiment of the process according to the present invention, in order to stabilize the single strand configuration in the region of the sequences TEM 1 and TEM 2 of the template nucleic acid, blocking oligonucleotides P4 and P5 are hybridized in the regions adjacent to TEM 1 and TEM 2. The TEM 3 region is preferably located at a distance of 2–50 nucleotides and particularly preferably 3–10 nucleotides from TEM 1. The TEM 4 region should be at a distance of 2–50, preferably 3–10 nucleotides from the binding site TEM 2. The oligonucleotides P4 and P5 preferably contain a modification, for example dideoxyribonucleotides, to block polymerase activity at the 3' end, in order to prevent elongation of P4 or P5. The oligonucleotides P4 and P5 are preferably 6–50 and particularly preferably 12–30 nt long.

In a further embodiment TEM 2 is at a distance of 1–1500, preferably of 1–150 nt from the 5' end of the TEM 1 region. The gap a between P2 and P3 can be filled up with a RNA-dependent or DNA-dependent DNA polymerase (optionally with RNAse H activity) and dNTP in the reaction mixture. In a further embodiment P1 and P2 contain phosphate residues at the 5' end and, after formation of the transcribable complex K, are linked together or/and to P3 by a ligase reaction (e.g. with T4 ligase, *E. coli* ligase or thermostable ligases).

In a further embodiment the 5' end of P1 protrudes by a sequence X beyond the transcription starting point. In this case a further oligonucleotide P6 is preferably used which is as long as X, preferably 10–40 nt, particularly preferably 15–25 nt. The function of P6 is that during the RNAse digestion the RNA region corresponding to X is digested and that no cDNA is formed for X and as a result the cDNA can hybridize with P1 directly adjacent to the 5' end of P1. Thus there is a nick between both oligonucleotides but there is no 3' protrusion of the cDNA.

The present invention in addition concerns a process for the specific detection of nucleic acids which includes the process according to the present invention for the specific production of nucleic acids and its embodiments in which the transcripts R or their secondary products are detected as a measure for the amount or presence of the template nucleic acid in the sample. In this connection secondary products are in particular understood as the intermediate products of the cyclical transcription reaction such as e.g. cDNA. The detection of these products can in principle be carried out in a known manner, for example by hybridization with labelled probe nucleic acids and detection of labelled hybrids. Another simple method is the incorporation of labelled mononucleotides during the transcription reaction and the separation of the reaction products by gel electrophoresis. This is especially facilitated by the fact that the products formed have a uniform length.

A particularly preferred embodiment of the process according to the present invention utilizes the incorporation of a detectably-labelled monoribonucleotide during the process of transcription (i.e. into the transcripts or/and their secondary products) and subsequent hybridization with a capture probe which is either bound directly to a solid phase or can be immobilized preferably by coupling to a chemical group such as e.g. biotin. In the case of immobilizable probes it is possible to subsequently immobilize on a solid phase which has a binding affinity to the chemical group. The label on the solid phase is preferably detected after separating the detectably-labelled mononucleotide. Digoxigenin (EP-A-0 324 474) is preferably used as the detectable group. The presence of this group on the solid phase is then detected by means of an enzyme-labelled antibody against digoxigenin.

Sequences are preferably selected for the capture or detection probe which are complementary or homologous to partial sequences or to the whole sequence of P3 (or if desired P7 . . . PN) or are complementary or homologous to the 5' region of P2 and 3' region of P3 (in each case preferably 6–25 nt, particularly preferably 8–13 nt). The entire probe is 6–5000 nt preferably 12–50 nt and particularly preferably 16–26 nt long. In the filling up reaction (example 7) these sequences are particularly preferably located in the region between P2 and P3 (filling up region); this results in an advantage for the specificity of the detection.

In a further embodiment P3 (or, if desired, P7 . . . PN) is labelled with a group capable of immobilization which is preferably at the 5' end. The cDNA can be bound via this group to a solid phase. With this P3 capable of immobilization, the complex K can also be bound to a surface before the transcription reaction. In this way a particularly effective removal of unspecific nucleic acids is achieved by a subsequent washing step. In this case after binding to the solid base, tetranscription reaction is started by addition of the enzymes and the oligonucleotides P1 and P3. The bound cDNA can either be detected by means of a labelled detector probe or by incorporation of detectably-labelled mononucleotides during the transcription. The cDNA which is coupled to the immobilizable group on the solid phase can, in an alternative embodiment, also be purified of all unspecific transcription products by washing.

Subsequently the amplification reaction is started by again adding enzymes/P1 and non-immobilizable P3.

In another embodiment the hybrid of template nucleic acid and immobilizable P3 is firstly bound to a solid phase. Subsequently P1 and P2 are added after a washing step. After hybridization of P1 and P2 to the P3/template hybrid, it is washed again and the immobilized complex K is transcribed by addition of RNA polymerase, P1 and non-immobilizable P3. The further reaction is carried out as described above.

In a further embodiment, P1 is immobilizably-modified. Then the transcription complex K or/and L can for example be bound to a solid phase and determined e.g. by means of labelled mononucleotides incorporated in G whose amount is a measure for the presence of template nucleic acid.

The detection method according to the present invention has all the advantages of the process for the production of nucleic acids according to the present invention.

Examples of detection methods are shown in each of the figures. However, these are also production processes according to the present invention when the detection steps are omitted.

The invention also concerns reagents and reagent kits for carrying out the processes according to the present invention.

The invention concerns a reagent which contains the following components:

a promoter oligonucleotide P1 which contains a single-stranded oligonucleotide binding site OBS in addition to the double-stranded promoter sequence PRO and at least one template-specific oligonucleotide P2, which contains a nucleotide sequence which is essentially complementary to OBS in addition to the specific sequence.

The reagent in addition preferably contains at least one of the aforementioned oligonucleotides P3, P4, P5 and P6, but particularly preferably at least P3. The preferred ratios of the amounts of oligonucleotides are referred to in the details of the processes according to the present invention. It also preferably contains the four types of mononucleoside triphosphates which are either unmodified or detectably or immobilizably modified. Furthermore it can contain pH buffers and auxiliary substances e.g. enzymes or stabilizers, in particular those substances which are suitable for the subsequent transcription reactions.

Double strand stabilizing agents can for example also serve as stabilizers, preferably a ligase, particularly preferably T4 ligase. A substantial increase in the efficiency of the transcription is achieved by these agents even if it is not possible to ligate the oligonucleotides together under the reaction conditions e.g. if the 5' ends of the oligonucleotides (for example P1, P2 or/and P3) are not phosphorylated.

In addition the invention concerns a reagent kit which contains in separate containers:

1) the promoter oligonucleotide P1, the template-specific oligonucleotide P2 and monoribonucleoside triphosphates;
2) a suitable transcription enzyme for the promoter
3) a reverse transcriptase; and
4) an enzyme that digests RNA.

The reagent kit can also contain the constituents stated in 1) separated from one another. Container 1 also preferably already contains the oligonucleotide P3 and, if desired, the monodeoxyribonucleoside triphosphates. However, they can also be in container 3 or in their own container.

In addition the reagent kit can contain control nucleic acids and/or reagents for preparing the samples.

If the reagent kit is to be used for the detection of nucleic acids or nucleotide sequences it preferably contains the reagents which are necessary for this in a separate container e.g. capture or/and detection probes.

BRIEF DESCRIPTION OF DRAWINGS

FIG. 2 (comprising FIG. 2a and FIG. 2b) shows a process in which a single strand stabilizing oligonucleotide P4 is also used. In addition the side reaction by reverse transcriptase is shown in the left part of this figure.

The transcription cycles are illustrated in FIG. 2 using the incorporation of detectably-labelled monodeoxyribonucleoside triphosphates (e.g. digoxigenin-dUTP) as an example. It also shows that the labelled cDNA can be detected by subsequent hybridization with a biotinylated capture probe and binding of the hybrid formed to a streptavidin solid phase.

Figure 3B:
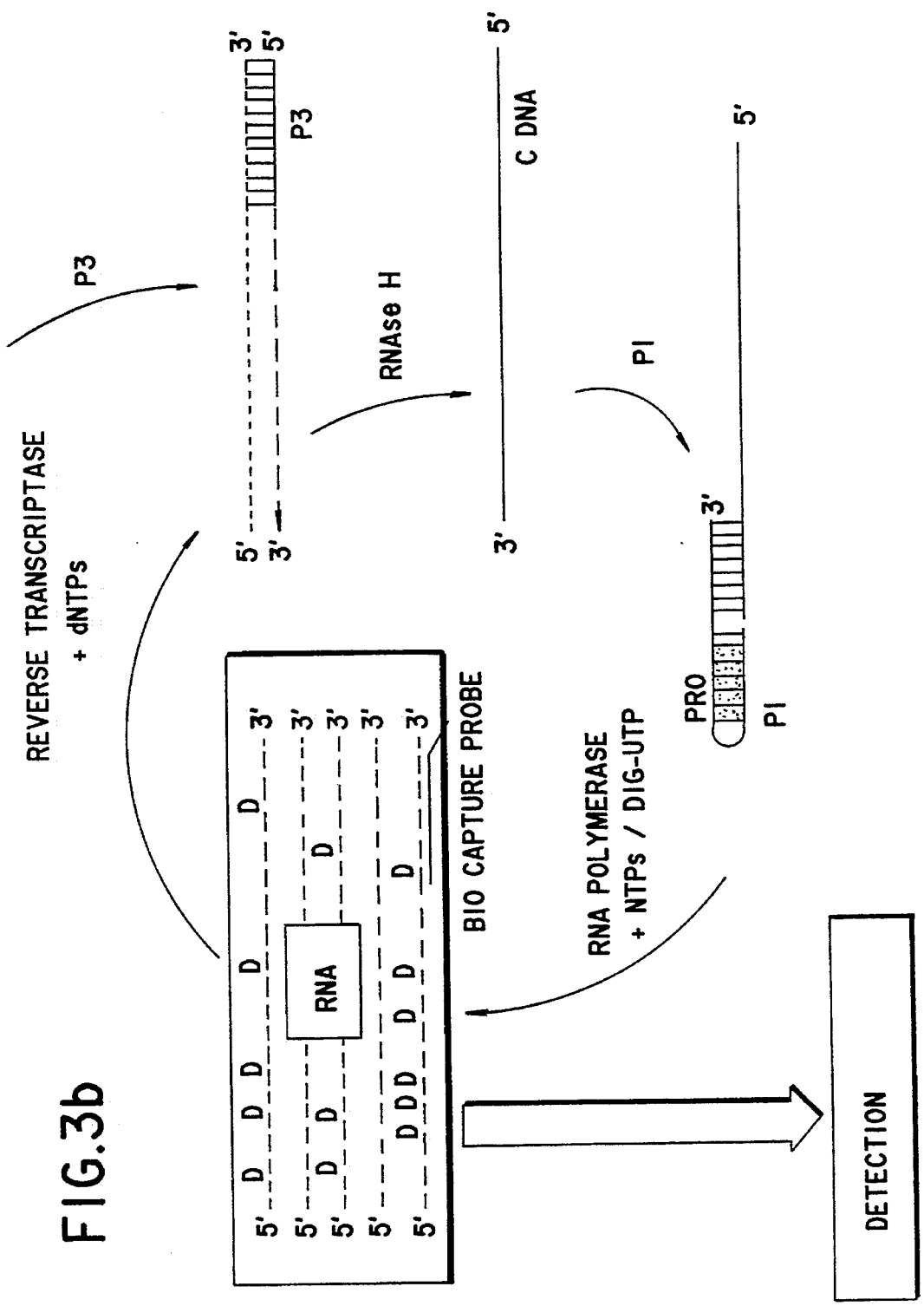

FIG. 3 (comprising FIG. 3a and FIG. 3b) shows an embodiment of the method of detection according to the present invention in which detectably labelled monoribonucleoside triphosphates (e.g. digoxigenin-UTP) are incorporated and the transcripts R are trapped by means of a biotinylated capture probe.

FIG. 4 (comprising FIG. 4a and FIG. 4b) shows an embodiment in which the single strand stabilizing oligonucleotides P4 and P5 as well as an immobilizable substituted oligonucleotide P3 are used. In this embodiment the cDNA is detected which is detectably as well as immobilizably-labelled.

An embodiment is shown in FIG. 5 (comprising FIG. 5a and FIG. 5b) in which, after formation of the nucleic acid complex K, a single-stranded region a is firstly filled up between oligonucleotide P2 and oligonucleotide P3 by means of DNA polymerase before the transcription is carried out.

Figure 6:
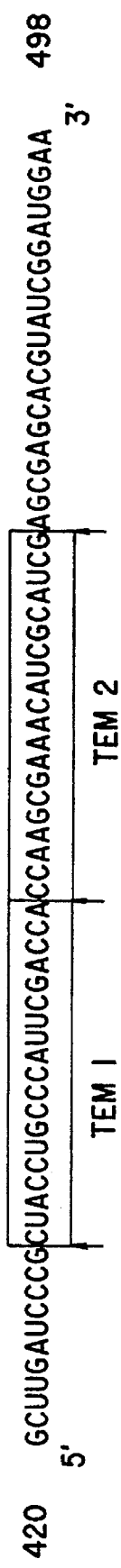

FIG. 6 shows the relevant part of a template nucleic acid. It is the plasmid pSPT18neoxEco R1. The regions in which oligonucleotide P2 and oligonucleotide P3 can hybridize are indicated.

Figure 7:
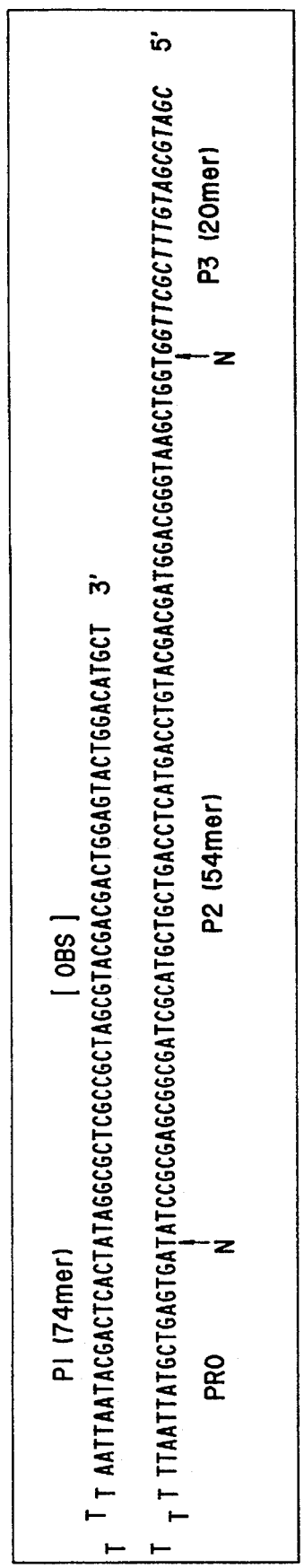
Figure 8:
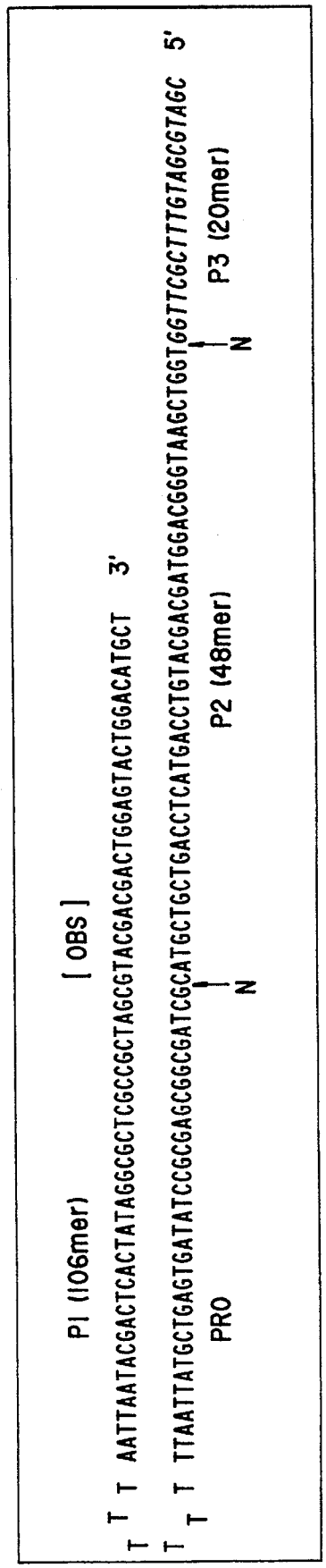

The nucleotide sequences for oligonucleotides P1, P2 and P3 are given in FIG. 7 and 8 for two different embodiments.

FIG. 7 shows a case in which P1 is a hairpin oligonucleotide having 74 nucleotides and the 5' end of P1 is located three nucleotides from the transcription starting point within the sequence PRO.

FIG. 8 shows the case in which P1 comprises 106 nucleotides and the 5' end is located 16 nucleotides from the transcription starting point and outside the sequence PRO.

Figure 9A:
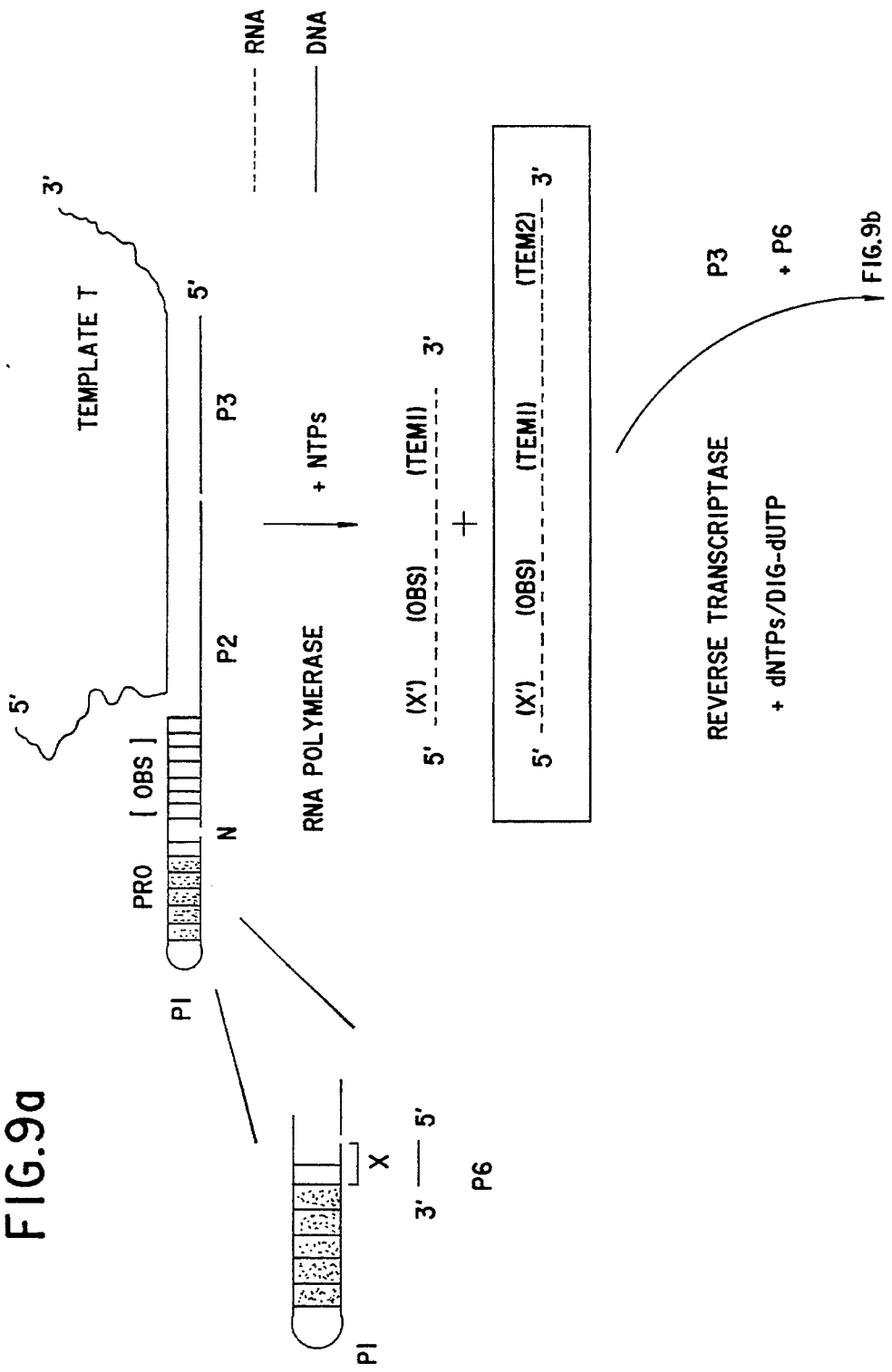

FIG. 9 (comprising FIG. 9a and 9b) describes the use of the oligonucleotides according to FIG. 7 in which, however, an oligonucleotide P6 is additionally added which is complementary to the region of P1 which protrudes beyond the transcription starting point. The effect of using oligonucleotide P6 is that the region of the transcripts designated X' is not transcribed into cDNA so that the cDNA can hybridize with P1 without a protrusion.

Figure 10A:
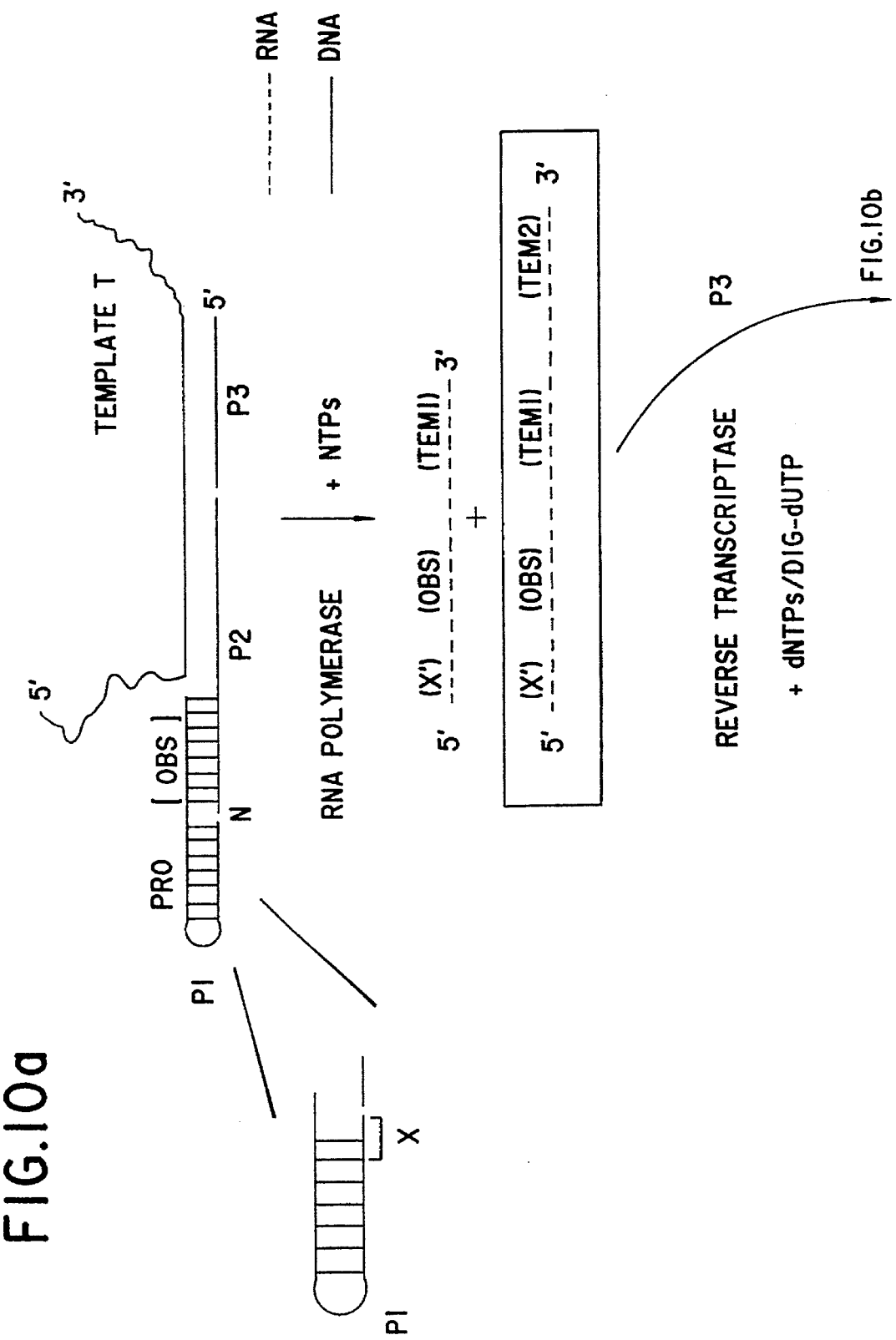
Figure 10B:
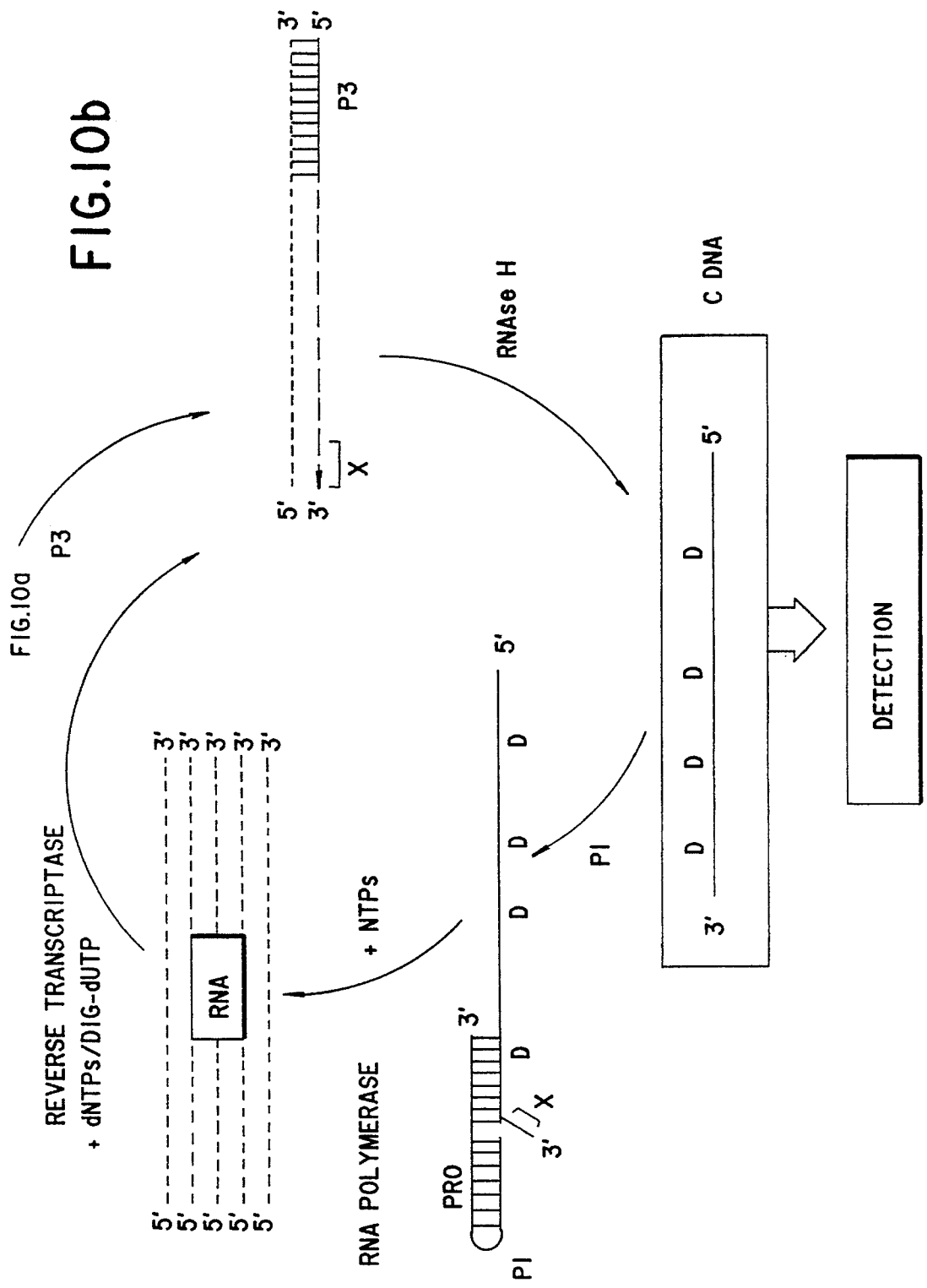

FIG. 10 (comprising FIG. 10a and FIG. 10b) describes the same case as FIG. 8 in which, however, the addition of an oligonucleotide P6 has been omitted. The protrusion X of the cDNA formed does not, however, interfere with the transcription reaction.

FIG. 11 shows P1 of example 2.

Figure 12:
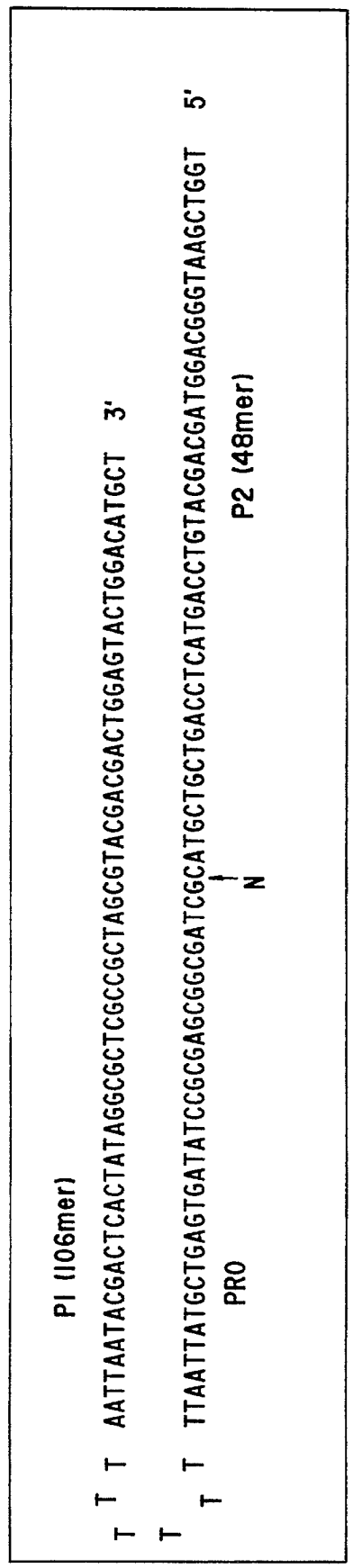

FIG. 12 shows the hybrid of P1 and P2 of example 3.

Figure 13:
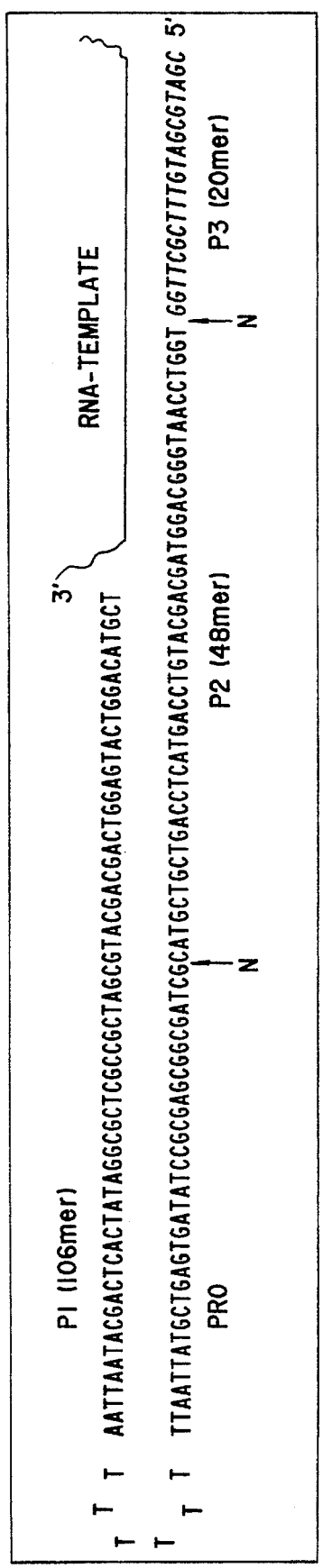

FIG. 13 shows the transcribable complex K of example 4.

Figure 14:
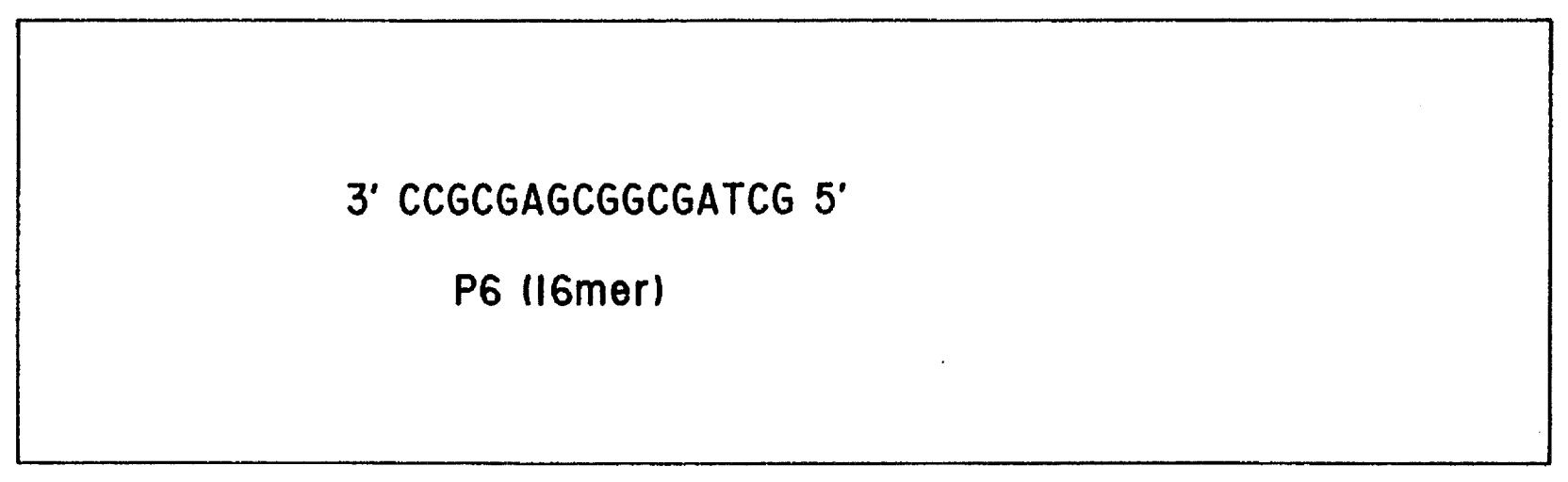

FIG. 14 shows the nucleotide sequence of P6 of example 5.

Figure 15:
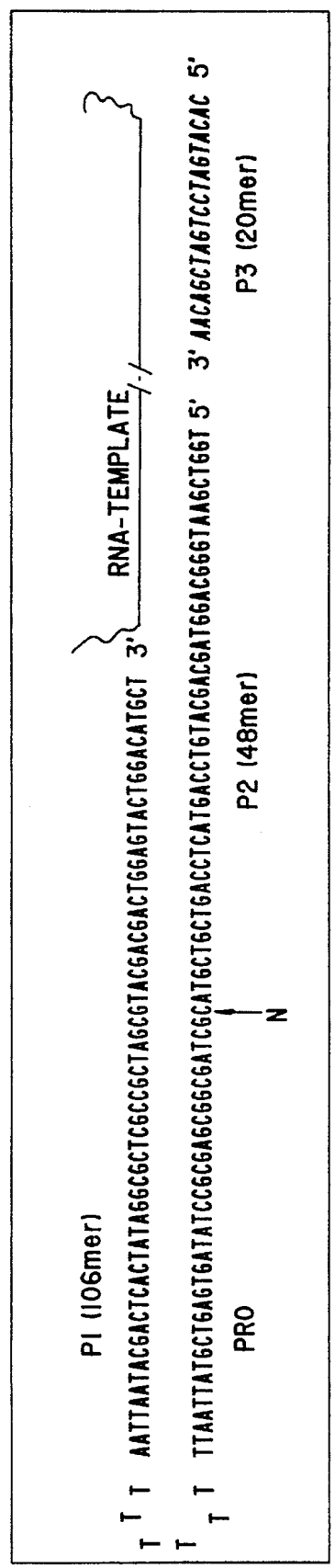

FIG. 15 shows the transcribable complex K in the event that the 3' end of P3 is separated from the 5' end of P2 by a gap.

List of abbreviations

| P | template-specific promoter reagent |
| T | template nucleic acid |
| K | transcribable nucleic acid complex of P and T or P, P3 and T |
| K' | transcribable nucleic acid complex of P1 and P2 (side product) |

-continued

List of abbreviations

| L | transcribable complex of P1 and G |
| R | transcript (RNA) |
| P1 | promoter oligonucleotide |
| P2 | template-specific oligonucleotide |
| P3 | primer oligonucleotide |
| P4 | oligonucleotide complementary to TEM 3 |
| P5 | oligonucleotide complementary to TEM 4 |
| P6 | oligonucleotide complementary to X |
| PRO | promoter region (double-stranded) |
| OBS | oligonucleotide P2 binding site |
| OBS' | sequence of P2 which can hybridize with all of OBS |
| TEM 1 | region on the template nucleic acid which is located nearest the transcription starting point |
| TEM 2 | region on the template nucleic acid which is located farthest away from the transcription starting point |
| TEM 1' | template-specific region of P2 |
| TEM 2' | template-specific region of the oligonucleotide P3 |
| TEM 3 | nucleotide region upstream of TEM 1 |
| TEM 4 | nucleotide region downstream of TEM 2 |
| X | nucleotide sequences downstream of the transcription starting point |
| X' | sequence complementary to X |
| G | opposite strand |
| RT | reverse transcriptase |
| BIO | biotin |
| D or DIG | digoxigenin |
| NTP | ribonucleoside triphosphate |
| dNTP | deoxyribonucleoside triphosphate |
| a | filling up region |
| a' | sequence complementary to the filling up region |
| N | single strand break (nick) |

The invention is elucidated in more detail by the following examples.

EXAMPLE 1

Production of RNA templates

Plasmid pSPT18 (sequence cf. WO 89/06698) is used for the production of transcripts of the neomycin resistance gene (neo). The neomycin gene (an aminoglycoside-3'-phosphotransferase II) is inserted into pSPT18 as described by Beck et al. (1982), Gene, 19, 327–336. Transcripts of the gene in the sense orientation can be produced from the resulting plasmid pSPT18neo using SP6 RNA polymerase. Plasmid pSPT18neo is linearized with the restriction endonuclease EcoRI. RNA transcripts, 1028 nucleotides in length, are produced from this linearized plasmid by in vitro transcription as described in Biochemicals for Molecular Biology, Boehringer Mannheim (1990), page 158. Position 1 of the transcript marks the SP6 RNA polymerase transcription starting point or the first nucleotide of the transcript. After phenol extraction to remove enzymatic components and ethanol precipitation, the transcripts purified in this way can be used in the following examples as templates.

EXAMPLE 2

Transcription on primer P1 (promoter construct with loop structure)

a) Production of the promoter-primer P1

P1 consists of a nucleic acid strand of 106 nt in which 28 nt at its 3' end correspond to the complementary sequence at the 3' end of P2. In addition P1 contains the minimal necessary self-complementary sequence of the promoter for the RNA polymerase of the bacteriophage T7 (sequence cf.

P1 in FIG. 12) (J. F. Milligan et al. (1987), Nucl. Acids Res., Vol. 15, No. 21, 8783–8798). These self-complementary sequences are separated from one another by an AT rich region which promotes the formation of the partial double strand in solution. In addition P1 contains additional transcribable self-complementary but not template-complementary sequences at the 5' end downstream of the promoter which promote the transcription as described by J. F. Milligan et al. (1987), Nucl. Acids Res., 15, p. 8783–8798.

After synthesis in a DNA synthesizer the DNA oligonucleotide of 106 nucleotides corresponding to P1 is purified by electrophoresis in a 20% denaturing polyacrylamide gel as described in Molecular Cloning (1989), Editors Sambrook, Fritsch, Maniatis, CSH, pages 6.39–6.48. In order to enable an annealing of the self-complementary sequences in P1 which is as complete as possible, this DNA oligonucleotide is heated to 90° C. for 10 minutes in a reaction vessel after the purification and subsequently it is cooled on ice for 10 minutes. P1 is examined for its ability to produce RNA transcripts in the presence of T7 RNA polymerase under the experimental conditions described in the following.

b) Transcription reaction

The reaction mixture contains the following in a final volume of 25 μl:

40 mmol/l Tris-HCl (pH 8.0 at 37° C.), 6 mmol/l MgCl$_2$, 10 mmol/l NaCl, 10 mmol/l dithiothreitol (DTT), 2 mmol/l spermidine-HCl, 5% (v/v) polyethylene glycol MW 6000, 0.01% (V/V) Triton X-100, 2 mmol/l each of ATP, UTP, GTP, CTP (pH 8.0 at 37° C.), 5 μCi [$^{32}$P]-CTP (400 Ci/mmol, Amersham), 500 nmol/l primer 1, 15 U/μl T7 RNA polymerase (Boehringer Mannheim), 1 U/μl RNAse inhibitor (Boehringer Mannheim).

The non-enzymatic materials used are treated before use with 0.01% diethylpyrocarbonate as described in Molecular Cloning (see above) pages 7.3–7.4.

The individual components are mixed in a reaction vessel of 100 μl volume and the preparation is incubated for one hour at 37° C.

c) Detection

Subsequently the reaction is stopped by addition of an equal volume of formamide stop buffer (95% formamide, 25 mM EDTA, 0.01% xylene cyanol, 0.01% bromophenol blue), heating for 3 minutes to 68° C. and cooling the reaction mixture on ice. An aliquot of the denatured reaction preparation is then applied to a 7M urea, 12% polyacrylamide gel with a layer thickness of 0.8 mm. The gel electrophoresis is carried out according to U.K. Laemmli (1970), Nature, 277, p. 680–685. The gel is subsequently autoradiographed and the radioactive products are analyzed.

The reaction can also be stopped by addition of 10 mmol/l EDTA and 0.1% SDS. For the detection the transcription products are then separated in a 1.5% denaturing agarose gel as described in Molecular cloning (see above), pages 7.43–7.45 and the reaction products are visualized by staining in an acridinium orange solution (5 μg/ml).

If no [$^{32}$P]-CTP is added to the reaction mixture, the specific reaction products can, after gel electrophoresis in polyacrylamide gels, be transferred to a nylon membrane by Northern blotting, immobilized by UV and detected by in-situ hybridization with complementary, radioactively or non-radioactively labelled (Biochemicals for Molecular Biology, see above, p. 112–115) DNA oligonucleotides. This type of hybridization is described by J. Meinkoth and G. Wahl (1984), Anal. Biochem., 138, p. 267–284 and in Nucleic Acid Hybridisation (1985) Editors B. D. Hames and S. J. Higgins, IRL Press, Oxford, p. 139–159.

After separation from non-incorporated [$^{32}$P]-CTP by gel filtration on a Sephadex G-50 column, the reaction products can also be detected by concentrating by ethanol precipitation and by dotting onto a nylon membrane, UV immobilization, exposure of an X-ray film to the dried membrane and measurement of the resulting blackening of the film.

By incorporation of non-radioactively labelled NTPs instead of [$^{32}$P]-CTP the products can be visualized directly in DOT, SLOT or Northern blot. The incorporation of digoxigenin-11-UTP or biotin-16-UTP (cf. WO 89/06698) can be used for direct detection with anti-digoxigenin-AP conjugate or with streptavidin-AP conjugate.

The detection is visualized by reaction of alkaline phosphatase (AP) with the corresponding substrate 5-bromo-4-chloro-3-indolyl phosphate (X-phosphate) and nitroblue tetrazolium salt (NBT), via the change in colour of the reaction solution as described in Biochemicals for Molecular Biology (see above) p. 109–115 or by a chemiluminescence reaction mediated by alkaline phosphatase using 3-(2'-spiroadamantan)-4-methoxy-4-(3''-phosphoryloxy)-phenyl-1,2-dioxetan (AMPPD$^R$, Boehringer Mannheim) as described by I. Bronstein and P. McGrath (1989), Nature, 338, p. 599–600.

The sensitivity of the chemiluminescence reaction can be increased further by addition of 5.6 μmol/15-N-tetradecanoylaminofluorescein (fluorescence enhancer) in 0.75 mol/l 2-amino-2-methyl-1-propanol buffer, pH 9.6 as described by M. Musani et al. (1991) Anal. Biochem., 194, p. 394–398. The light emission caused by the chemiluminescence reaction is documented by exposing a Polaroid or an X-ray film.

RNA is produced which extends from the transcription start on the promoter up to the 5' end of the oligonucleotide P1.

EXAMPLE 3

Transcription of the hybrid of P1 and P2 a) Production of P2

P2 is composed of a nucleic acid strand of 48 nt in which 28 nt at its 3' end correspond to the complementary sequence at the 3' end of P1 (sequence cf. FIG. 13). In addition P2 contains at its 5' end 20 nt which are complementary to the ribonucleotide positions 431–450 of the RNA transcript described in example 1 or are complementary to the nucleotide positions 1935–1954 of the sequence which according to Beck et al contains the neogene (see above). The DNA oligonucleotide of 48 nucleotides corresponding to P2 is purified after the synthesis as described in example 2.

b) Transcription reaction

The transcription reaction is carried out under the same conditions as in example 2.

In order to enable an annealing of the complementary sequences of P1 and P2 which is as complete as possible, equimolar amounts of these DNA oligonucleotides are heated to 90° C. for 10 minutes in a reaction vessel before addition of the other reaction components and cooled for 10 minutes on ice. Subsequently the denatured DNA oligonucleotides are hybridized for 10 minutes at 37° C. The transcription buffer and the enzymatic components (see example 2) are mixed in a reaction vessel and the prehybridized oligonucleotides P1 and P2 are each added at a final concentration of 500 nmol/l. The reaction mixture is incubated for one hour at 37° C.

Subsequently the reaction products are detected as described in example 2 and the RNA products are analyzed.

RNA is produced which extends from the transcription start on the promoter within P1 up to the 5' end of P2.

EXAMPLE 4

Transcription of a hybrid of P1, P2, P3 with a RNA template or an oligonucleotide template or a plasmid template.

a) Production of P3 and the oligonucleotide template

The sequence of P3 (DNA oligonucleotide of 20 nucleotides; sequence cf. FIG. 14) is complementary to the ribonucleotide positions 451–470 of the RNA transcript described in example 1 or to the nucleotide positions 1955–1974 of the sequence described by Beck et al. (see above) which includes the neogene. This complementary sequence is chosen so that the 3' end of P3 can hybridize with the RNA template directly adjacent to the 5' end of P2. The DNA oligonucleotide of 20 nucleotides corresponding to P3 is purified after the synthesis as described in example 2. The sequence of the oligonucleotide template (DNA oligonucleotide of 38 nucleotides) is homologous to the ribonucleotide positions 431–468 of the RNA transcript described in example 1. This homologous sequence to the RNA transcript is chosen so that the template complementary regions of P2 and P3 hybridize directly adjacent on the oligonucleotide template.

b) Transcription reaction

The transcription reaction is carried out as in examples 2–3. In order to enable an annealing of the complementary sequences of P1, P2, P3 and the RNA template which is as complete as possible, these DNA oligonucleotides are heated to 90° C. for 10 minutes in a reaction vessel before addition of the other reaction components and cooled for 10 minutes on ice. This denaturation step also prevents the formation of possible secondary structures within the RNA template. Subsequently the components are hybridized for 10 minutes at 37° C. An oligonucleotide template, which contains at least the neo sequence from 1935 to 1972, can be used instead of a RNA template for hybridization with P2 and P3. The transcription buffer and the enzymatic components (see example 2) are mixed in a reaction vessel and the prehybridized oligonucleotides P1, P3 and RNA template are each added at a final concentration of 500 nmol/l and P2 is added at a final concentration of 50 nmol/l. The reaction mixture is incubated for one hour at 37° C.

Subsequently the reaction products are detected as described in example 2 and the RNA products are analyzed. RNA is produced which extends from the transcription start on the promoter within P1 up to the 5' end of the primer P3.

EXAMPLE 5

Amplification by transcription of a hybrid of P1, P2, p3and of a RNAtemplate oran- oligonucleotide template in the presence of P6, reverse transcriptase and RNAse H a) Production of P6

The sequence of P6 (DNA oligonucleotide of 16 nucleotides; sequence cf. FIG. 15) is homologous to the nucleotide positions 1–16 of P1. This homologous sequence is chosen so that it can completely hybridize with the transcript produced in example 2. In the amplification reaction described in the following this partial RNA/DNA hybrid represents a substrate for the RNAse H.

The DNA oligonucleotide of 16 nucleotides corresponding to primer 6 is purified after the synthesis as described in example 2.

The plasmid pSPT18 neo is also used for the describe reaction and was heated to 95° C. before hybridization with P1, P2 and P3.

b) Amplification reaction

The amplification reaction is carried out in the same way as the transcription reaction in examples 2–4 with the following changes: The reaction mixture, however, contains no RNAse inhibitor and in addition dATP, dCTP, dGTP and dTTP are added at a concentration of 1 mmol/l, AMV reverse transcriptase (Boehringer Mannheim GmbH) at a concentration of 0.4 U/µl and RNAseH (Boehringer Mannheim GmbH) at a concentration of 0,005 U/µl .

In order to enable an annealing of the complementary sequences of the primers P1, P2, P3 and the RNA template or the oligonucleotide template which is as complete as possible the oligonucleotides are denaturatedas described in examples 2– 4 before addition of the other components. The transcription buffer and enzymatic components are mixed in a reaction vessel and the denatured oligonucleotides P1, P3 and P6 are each added at a final concentration of 500 nmol/l, primer P2 is added at a final concentration of 50 nmol/l and the RNA template or the oligonucleotide template at a final concentration of 100–$10^6$ molecules per reaction mixture. The reaction mixture is incubated for two hours at 37° C.

Subsequently the reaction products are detected as described in example 2 and the RNA products are analyzed.

RNA can be detected which extends from the 3' end of P2 up to the 5' end of P3.

EXAMPLE 6

Amplification by transcription of a hybrid of P1, P2, P3 and RNA template or oligonucleotide template in the presence of P6, reverse transcriptase, and RNAse H, labelling the cDNA during synthesis by incorporation of digoxigenin-11-dUTP and subsequent separation of the specific cDNA reaction products via a biotin-labelled complementary oligonucleotide on a solid phase.

a) Production of the biotin-labelled oligonucleotide

The sequence of the biotin-labelled oligonucleotide with a length of 27 nucleotides is complementary to the nucleotide positions 1–10 of P2 and to the nucleotide positions 11–20 of P3. The other 7 nucleotides are not complementary to sequences of the RNA template. The sequence is chosen so that it can only hybridize with specific reaction products under the hybridization conditions described in the following. The biotin labelling of the oligonucleotide is described in EP-A-0 097 373.

b) Amplification reaction

The amplification reaction is carried out as described in example 5 with the following changes: The reaction mixture, however, does not contain [$^{32}$P]-CTP. The dTTP concentration is 0.66 mmol/l and in addition digoxigenin-11-2'-deoxyuridine-5'-dUTP (DIG-[11]-dUTP, Boehringer Mannheim) is added at a final concentration of 0.33 mmol/l (cf. WO 89/06698).

c) Detection

After the amplification reaction the products are separated from non-incorporated nucleotides as described in example 2 by gel filtration on Sephadex G-50. Subsequently the products are denatured by incubating for 10 minutes at 92° C. and incubated for 4 hours at 45° C. with 20 ng of the biotin-labelled oligonucleotide in 200 μl with 10% formamide, 5x SSC, 1x Denhardt's solution and 50 mmol/l sodium phosphate, pH 6.8 in a well of a streptavidin-coated microtitre plate (produced according to EP-A-0 344 578). In this process the final concentration of the biotin-labelled oligonucleotide is 8 nmol/l. After hybridization/binding to the wall, it is washed twice for 10 minutes at 37° C. with 200 μl 0.3 mol/l NaCl, 0.003 mol/l sodium citrate, 0.2% SDS and once briefly at room temperature with 0.9% NaCl. After the addition of 200 mU/ml anti-digoxigenin antibody-horseradish peroxidase conjugate in 100 mmol/l Tris-HCl (pH 7.5), 0.9% NaCl, 1% BSA it is incubated for 30 minutes at 37° C. while shaking. Non-bound conjugate is removed by washing 3 times with 0.9% NaCl at room temperature. After incubating for 30 minutes at 37° C. with 1.9 mmol/l 2,2'-azino-di[3-ethyl-benzthiazoline sulfonic acid]-(6)-diammonium salt (ABTS$^R$, Boehringer Mannheim) the absorbance is measured at 405 nm by means of an ELISA reader.

The detection can be carried out directly via the test with anti-digoxigenin AP conjugate or streptavidin AP conjugate as described in example 2 but in this case after the incorporation of digoxigenin-11-dUTP or biotin-16-dUTP during the cDNA synthesis, subsequent Southern blot on a nylon membrane and subsequent UV immobilization.

EXAMPLE 7

Amplification by transcription of a hybrid of P1, P2, P3 and RNA template in the presence of P6, reverse transcriptase and RNAse H a) Production of P3

The sequence of P3 (DNA oligonucleotide of 20 nucleotides; sequence cf. FIG. 16) is complementary to the ribonucleotide positions 501–520 of the RNA transcript described in example 1 or to the nucleotide positions 2005–2024 of the sequence described by Beck et al. (see above) which includes the neogene. This complementary sequence is chosen so that the 3' end of P3 can hybridize with the RNA template described in example 1 at a distance of 50 nucleotides from the 5' end of primer 2. The DNA oligonucleotide of 20 nucleotides corresponding to P3 is purified after the synthesis (see example 2).

b) Amplification reaction

The amplification reaction and the detection is carried out as described in example 5 or in example 6 with the following changes: The reaction mixture contains P1, P3, P6 at a final concentration of 500 nmol/l and P2 at a final concentration of 50 nmol/l.

The RNA product or cDNA product synthesized in the amplification reaction can also be specifically detected via hybridization with a complementary biotin-labelled oligonucleotide as described in example 2 and 6. In this process the sequence of this biotin-labelled oligonucleotide is chosen so that its hybridizable region is complementary to the region of the RNA or cDNA which is synthesized during the amplification between P2 and P3.

RNA can be detected as described in example 5 or cDNA as described in example 6 which extends from the 3' end of P2 to the 5' end of P3.

EXAMPLE 8

Range of variation of the reaction

Reaction conditions are given in the following within which the process according to the present invention proceeds. However, on the basis of a few experiments a person skilled in the art can also determine conditions which differ from this.

|  | Optimal conditions | Range of variation |
| --- | --- | --- |
| Tris-HCl | 40 mM (pH 8.0) | 2–150 mM (pH 7.5–8.5) |
| MgCl$_2$ | 6 mM | 2–20 mM |
| NaCl | 10 mM | 0–200 mM |
| DTT | 10 mM | 0–20 mM |
| Spermidine-HCl | 2 mM | 0–10 mM |
| PEG 6000 | 5% | 2–10% |
| Triton X-100 | 0.01% | 0–0.5% |
| BSA | — | 0–100 μg/ml |
| RNAase inhibitor | 1 U/μl | 0–5 U/μl |
| dNTPs | 1 mM | 0.1–5 mM |
| NTPs | 2 mM | 0.2–5 mM |
| Primer 1/3/6 | 500 nM | 100 nM–1.5 μM |
| Primer 2 | 50 nM | 1–500 nM |
| RNA polymerases | T7 RNA polymerases | T7, SP6, T3, N4, RNA polymerases |
| T7 RNA polymerases | 15 U/μl | 5–25 U/μl |
| Reverse transcriptase | AMV reverse transcriptase | AMV or Mo-MLV reverse transcriptase |
| Reverse transcriptase | 0.4 U/μl | 0.2–10 U/μl |
| RNAse H | 0.005 U/μl | 0.001–0.05 U/μl |
| Reaction temp. | 37° C. | 35–42° C. |
| Reaction time | 60 min | 20 min–3 hours |
| Reaction volume | 25 μl | 20–200 μl |
| Prehybridization | 0–30 min. | 0–6 h |

We claim:

1. Process for the production of specific transcripts from a target nucleic acid template comprising the steps of:
   a) adding a promotor reagent P to a sample containing a target nucleic acid T, wherein at least part of nucleic acid T is in single stranded form or is converted to single stranded form, and wherein a nucleic acid complex K is formed in which the template nucleic acid is hybridized to a oligonucleotide P2 via a double-stranded region TEM 1/TEM 1' which is then hybridized to a promoter oligonucleotide P1 via a double-stranded region OBS/OBS', and
   b) forming transcripts R by promotor controlled transcription using said target nucleic acid T as a template,
   wherein the promotor reagent P contains a promotor oligonucleotide P1 and a separate template-specific oligonucleotide P2 which can hybridize with P1, and wherein the oligonucleotides P1 and P2 are not ligated together.

Figure 1A:
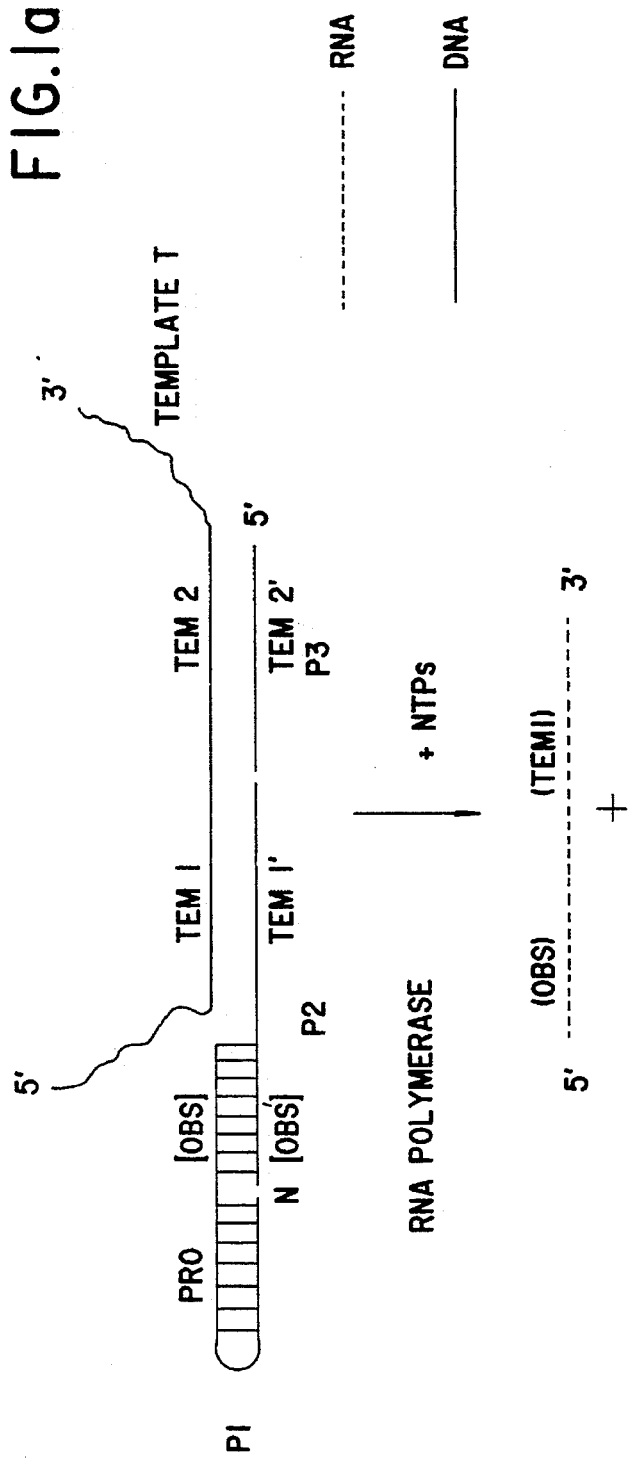
FIG. 1 (comprising FIG. 1a and FIG. 1b) shows a diagram of the detection method according to the present invention in the form of the preferred embodiment in which an oligonucleotide P3 is used.

2. The process according to claim 1, wherein the promotor reagent P further comprises at least one additional separate template-specific oligonucleotide P3 adjacent to said oligonucleotide P2 as shown in FIG. 1a.

3. The process according to claim 2, wherein the amount of oligonucleotide P3 used in the process is approximately equal to the amount of oligonucleotide P1 used in the process.

4. The process according to claim 2, wherein the oligonucleotides P2 and P3 are not ligated together in any phase of the process.

5. The process according to claim 2, wherein the nucleic acid complex K contains, in addition to the oligonucleotides P1, P2 and P3, at least one single-stranded stabilizing oligonucleotide hybridized to a region adjacent to the regions in which P2 and P3 are hybridized as shown in FIGS. 2a, 2b, 4a, and 4b.

6. The process according to claim 2, wherein the oligonucleotides P1 and P2 as well as P2 and P3 in the nucleic acid complex K are only separated by a nick.

7. The process according to claim 1, wherein the amount of oligonucleotide P2 contained in P is less than the amount of oligonucleotide P1 contained in P.

8. The process according to claim 1, further comprising the steps of:
   forming strands G which are complementary to the transcripts R,
   hybridizing said strands G with P1 to form hybrids H, and
   forming additional transcription products by transcription controlled by a promotor contained in P, using said strands G as templates as shown in FIG. 1b.

9. The process according to claim 8, further comprising the enzymatic digestion of the transcripts R after the formation of said G strands wherein said G strands remain as templates.

10. The process according to claim 1, wherein a polymerase which reads through single-stranded breaks is used for transcription.

11. Process for the detection of specific nucleic acids comprising the steps of:
   a) adding a promotor reagent P to a sample containing a template nucleic acid T, wherein at least part of nucleic acid T is in single stranded form or is converted to single stranded form, and wherein a nucleic acid complex K is formed in which the template nucleic acid is hybridized to the oligonucleotide P2 via a double-stranded region TEM 1/TEM 1', which is then hybridized to a promoter oligonucleotide P1 via a double-stranded region OBS/OBS', b) forming transcripts R by transcription controlled by a promotor contained in P, and c) detecting the transcripts R, a hybrid of R and cDNA, a cDNA, a hybrid of P1 and cDNA or a mixture of these products, wherein the promotor reagent P contains a promotor oligonucleotide P1 and a separate template-specific oligonucleotide P2 which can hybridize with P1 and wherein the oligonucleotides P1 and P2 are not ligated together.

12. The process according to claim 11, wherein the promotor reagent P further comprises at least one additional separate template-specific oligonucleotide P3 adjacent to said oligonucleotide P2 as shown in FIG. 1a.

13. The process according to claim 12, wherein the amount of oligonucleotide P3 used in the process is approximately equal to the amount of oligonucleotide P1 used in the process.

14. The process according to claim 12, wherein the oligonucleotides P2 and P3 are not ligated together in any phase of the process.

15. The process according to claim 12, wherein the nucleic acid complex K contains, in addition to the oligonucleotides P1, P2 and P3, at least one single-stranded stabilizing oligonucleotide hybridized to a region adjacent to the regions in which P2 and P3 are hybridized as shown in FIGS. 2a, 2b, 4a, and 4b.

16. The process according to claim 12, wherein the oligonucleotides P1 and P2 as well as P2 and P3 in the nucleic acid complex K are only separated by a nick.

17. The process according to claim 11, wherein the amount of oligonucleotide P2 contained in P is less than the amount of oligonucleotide P1 contained in P.

18. The process according to claim 11, further comprising the steps of:

forming strands G which are complementary to the transcripts R, hybridizing said strands G with P1 to form hybrids H, and forming additional transcription products by transcription controlled by a promotor contained in P using said strands G as templates as shown in FIG. 1b.

19. The process according to claim 11, wherein detectably labelled mononucleotides are incorporated into the transcripts R during transcription.

20. The process according to claim 11, further comprising hybridizing the transcripts R with a capture probe which can be immobilized.

21. The process according to claim 19, wherein said detectably labelled mononucleotides are labelled with digoxigenin.

22. The process according to claim 11, further comprising hybridizing the transcripts R or secondary products with labelled probe nucleic acids and detecting the resulting labelled hybrids.

23. The process according to claim 11, wherein a polymerase which reads through single-stranded breaks is used for transcription.

24. The process according to claim 23, wherein said polymerase is T7 RNA polymerase.

25. The process according to claim 10, wherein said polymerase is T7 RNA polymerase.

* * * * *